(12) United States Patent
Cabirol et al.

(10) Patent No.: US 10,196,667 B2
(45) Date of Patent: Feb. 5, 2019

(54) PROCESSES USING AMINO ACID DEHYDROGENASES AND KETOREDUCTASE-BASED COFACTOR REGENERATING SYSTEM

(71) Applicant: Codexis, Inc., Redwood City, CA (US)

(72) Inventors: Fabien Louis Cabirol, Dusseldorf (DE); Steven J. Collier, Concord, MA (US); Thomas Daussmann, Annweiler (DE); Naga K. Modukuru, Singapore (SG)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 15/627,652

(22) Filed: Jun. 20, 2017

(65) Prior Publication Data

US 2017/0292141 A1 Oct. 12, 2017

Related U.S. Application Data

(62) Division of application No. 15/184,242, filed on Jun. 16, 2016, now Pat. No. 9,714,439, which is a division of application No. 14/742,215, filed on Jun. 17, 2015, now Pat. No. 9,394,551, which is a division of application No. 13/577,772, filed as application No. PCT/US2011/024102 on Feb. 8, 2011, now Pat. No. 9,080,192.

(60) Provisional application No. 61/303,179, filed on Feb. 10, 2010.

(51) Int. Cl.

| C12P 13/04 | (2006.01) |
| C12N 9/02 | (2006.01) |
| C12N 9/08 | (2006.01) |
| C12P 41/00 | (2006.01) |
| C12P 13/06 | (2006.01) |
| C12N 9/04 | (2006.01) |
| C12N 9/06 | (2006.01) |
| C12P 7/40 | (2006.01) |

(52) U.S. Cl.
CPC .......... *C12P 41/007* (2013.01); *C12N 9/0004* (2013.01); *C12N 9/0006* (2013.01); *C12N 9/0016* (2013.01); *C12P 7/40* (2013.01); *C12P 13/04* (2013.01); *C12P 13/06* (2013.01); *C12Y 101/00* (2013.01); *C12Y 101/01* (2013.01); *C12Y 104/01009* (2013.01); *C12Y 104/99001* (2013.01)

(58) Field of Classification Search
CPC ........ C12P 13/04; C12P 13/06; C12N 9/0004; C12Y 104/01009
USPC ................. 435/128, 106, 189, 193
See application file for complete search history.

(56) References Cited

U.S. PATENT DOCUMENTS

| 5,559,030 A | 9/1996 | Matsuyama et al. |
| 5,700,670 A | 12/1997 | Yamagishi et al. |
| 5,854,035 A | 12/1998 | Stoyan et al. |
| 5,891,685 A | 4/1999 | Yamagishi et al. |
| 6,399,339 B1 | 6/2002 | Wolberg et al. |
| 6,645,746 B1 | 11/2003 | Kizaki et al. |
| 6,800,477 B2 | 10/2004 | Patel et al. |
| 7,083,973 B2 | 8/2006 | Patel et al. |
| 7,217,544 B2 | 5/2007 | Hummel et al. |
| 7,582,468 B2 | 9/2009 | Bowers et al. |
| 7,794,993 B2 | 9/2010 | Kizaki et al. |
| 7,915,022 B2 | 3/2011 | Kizaki et al. |
| 9,080,192 B2 | 7/2015 | Cabirol et al. |
| 9,394,551 B2 | 6/2016 | Cabirol et al. |
| 2004/0137585 A1 | 7/2004 | Davis et al. |
| 2005/0192439 A1 | 9/2005 | Rozzell et al. |
| 2006/0286646 A1 | 12/2006 | Patel et al. |
| 2008/0206826 A1 | 8/2008 | Meudt et al. |
| 2009/0087885 A1 | 4/2009 | Groeger et al. |
| 2009/0123983 A1 | 5/2009 | Niddam-Hildesheim et al. |
| 2009/0162909 A1 | 6/2009 | Campopiano et al. |
| 2010/0028959 A1 | 2/2010 | Kanamaru et al. |
| 2010/0248317 A1 | 9/2010 | Gupta et al. |
| 2011/0059503 A1 | 3/2011 | Taylor et al. |
| 2011/0250653 A1 | 10/2011 | Toda et al. |
| 2011/0281309 A1 | 11/2011 | Kanamaru et al. |

FOREIGN PATENT DOCUMENTS

| EP | 1925674 A1 | 5/2008 |
| EP | 0983372 B1 | 4/2010 |
| EP | 221294 A1 | 8/2010 |
| EP | 2345733 A1 | 7/2011 |
| EP | 2357248 A1 | 8/2011 |
| EP | 2374882 A1 | 10/2011 |
| EP | 2423187 A1 | 2/2012 |
| JP | 2009242288 A | 10/2009 |
| JP | 2009263278 | 11/2009 |
| WO | 1995022625 A1 | 8/1995 |
| WO | 1997020078 A1 | 6/1997 |
| WO | 1997035966 A1 | 10/1997 |

(Continued)

OTHER PUBLICATIONS

Alanvert, E et al., "Highly stereoselective biocatalytic reduction of alpha-halo ketones," Tetrahedron: Symmetry vol. 20: 2462-2466 (2009.

(Continued)

*Primary Examiner* — Robert B Mondesi
*Assistant Examiner* — Mohammad Y Meah
(74) *Attorney, Agent, or Firm* — Codexis, Inc.

(57) ABSTRACT

The present disclosure relates to the use of an amino acid dehydrogenase in combination with a cofactor regenerating system comprising a ketoreductase. In particular embodiments, the process can be used to prepare L-tert-leucine using a leucine dehydrogenase.

23 Claims, No Drawings
Specification includes a Sequence Listing.

(56) References Cited

FOREIGN PATENT DOCUMENTS

| WO | 1998027230 A1 | 6/1998 |
|---|---|---|
| WO | 2001007567 A1 | 2/2001 |
| WO | 2001075767 A1 | 10/2001 |
| WO | 2005018579 A2 | 3/2005 |
| WO | 2008038050 A2 | 4/2008 |
| WO | 2008131215 A2 | 10/2008 |
| WO | 2009040080 A1 | 4/2009 |
| WO | 2009042984 A1 | 4/2009 |
| WO | 2010050564 | 5/2010 |
| WO | 2010067578 A1 | 6/2010 |
| WO | 2010067613 A1 | 6/2010 |
| WO | 2010122682 A1 | 10/2010 |
| WO | 2011005527 A2 | 1/2011 |

OTHER PUBLICATIONS

Santaniello, E., et al., "Chiral Synthesis of a component of amanita muscaria, (−)4-hydroxypyrrolidin-2-one, and assessment of its absolute configuration," Journal Chemical Research, vol. 132:132-133 (1984).

Zhu, D. et al., "Green synthesis of important pharmaceutical building blocks: enzymatic access to enantiomerically pure α-chloroalcohols," Tetrahedron: Asymmetry 16:3275-3278 (2005).

Genbank No. YP_001165929 dated May 8, 2007.

Genbank No. ABP64403.1 dated Apr. 18, 2007.

Broussy, S. et al., "Enantioselective, Ketoreductase-Based Entry into Pharmaceutical Building Blocks: Ethanol as Tunable Nicotinamide Reductant," Organic Letters vol. 11:2:305*308 (2009).

Hong, E., et al., "Asymmetric synthesis of L-tert-leucine and L-3-hydroxyadamantylglycine using Branched Chain Aminotransferase," Journal Molecular Catalysis B: Enzymatic 66:228-233 (2010).

Johannes, T., et al., "Directed Evolution of a Thermostable Phosphite Dehydrogenase for NAD(P)H Regeneration," Applied and Enviornmental Microbiology, vol. 71:10 5728-5734 (2005).

Johannes, T., et al., "Efficient Regeneration of NADPH Using an Engineered Phosphite Dehydrogenase," Biotechnology and Bioengineering, vol. 96:18-26 (2007).

McLachlan, M., et al., "Further Improvement of Phosphite Dehydrogenase Thermostability by Saturation Mutagenesis," Biotechnology and Bioengineering, vol. 99:2 268-274 (2008).

Mihara, H., et al., "N-Methyl-L-Amino acid dehydrogenase from Pseudomonas putida," FEBS Journal, 272: 111791123 (2005).

Paradisi, F., et al., "Phenylalanine dehydrogenase mutants: efficient biocatalysts for synthesis of non-natural phenylalanine derivatives," Journal Biotechnology, 128:408-411 (2007).

Wang, X., et al., "Forced evolution of *Escherichia coli* cells with the ability to effectively utilize non-natural amino acids L-tert-leucine, L-norleucine and gamma-methyl-L-leucine," Biocatalysis and Biotransformation, 28:(5-6):293-303 (2010).

PCT International Search Report for International Appl. No. PCT/US2011/024102 dated Oct. 21, 2011.

SEQUENCE LISTING

<160> NUMBER OF SEQ ID NOS: 26

<210> SEQ ID NO 1
<211> LENGTH: 792
<212> TYPE: DNA
<213> ORGANISM: Artificial Sequence
<220> FEATURE:
<223> OTHER INFORMATION: Variant of ketoreductase from Novosphingobium aromaticivorans

<400> SEQUENCE: 1

```
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgt gcacaacgc gggcatctcg atcgtcacga agttcgaaga cactccgctg     300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgggggtct gcgcggcgcg gcgttcaatg cggcctattg caccagcaag     480
gcggcggtga agatgctctc gaagtgcctc ggcgcggaat cgcggcgct cggctacaac     540
atccgcgtca actccgtgca tccgggcggc atcgataccc cgatgctcgg ctcgatcatg     600
gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat cgtgatgga cggcggcttc     780
agccaggtct ga                                                         792
```

<210> SEQ ID NO 2
<211> LENGTH: 263
<212> TYPE: PRT
<213> ORGANISM: Novosphingobium aromaticivorans

<400> SEQUENCE: 2

```
Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Phe Asn Ala Ala Tyr Cys Thr Ser Lys
145                 150                 155                 160
```

```
Ala Ala Val Lys Met Leu Ser Lys Cys Leu Gly Ala Glu Phe Ala Ala
            165                 170                 175

Leu Gly Tyr Asn Ile Arg Val Asn Ser Val His Pro Gly Gly Ile Asp
        180                 185                 190

Thr Pro Met Leu Gly Ser Ile Met Asp Lys Tyr Val Glu Leu Gly Ala
    195                 200                 205

Ala Pro Ser Arg Glu Val Ala Gln Ala Ala Met Glu Met Arg His Pro
210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260

<210> SEQ ID NO 3
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 3
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgt gcacaacgc gggcatctcg atcgtcacga agttcgaaga cactccgctg      300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420 tttccagcg tcgtgggtct cgcgcggcgcg gcgttcaatg cggcctattg caccagcaag     480
gcggcggtga agatgctctc gaagtgcctc ggcgcggaat cgcggcgct cggctacaac     540 atccgcgtca actccgtgca tccgggcggc atcgatcccc gatgctcgg ctcgatcatg     600 gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat cgtgatgga cggcggcttc     780 agccaggtct ga                                                          792

<210> SEQ ID NO 4
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 4

Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45
```

```
Val Glu Gly Ala Asp His Tyr Leu Gln His Asp Val Thr Ser Glu Ala
 50                  55                  60

Gly Trp Lys Ala Val Ala Ala Leu Ala Gln Glu Lys Tyr Gly Arg Val
 65                  70                  75                  80

Asp Ala Leu Val His Asn Ala Gly Ile Ser Ile Val Thr Lys Phe Glu
                 85                  90                  95

Asp Thr Pro Leu Ser Asp Phe His Arg Val Asn Thr Val Asn Val Asp
                100                 105                 110

Ser Ile Ile Ile Gly Thr Gln Val Leu Leu Pro Leu Leu Lys Glu Gly
                115                 120                 125

Gly Lys Ala Arg Ala Gly Gly Ala Ser Val Val Asn Phe Ser Ser Val
130                 135                 140

Val Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
                180                 185                 190

Thr Pro Met Leu Gly Ser Ile Met Asp Lys Tyr Val Glu Leu Gly Ala
                195                 200                 205

Ala Pro Ser Arg Glu Val Ala Gln Ala Ala Met Glu Met Arg His Pro
210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
                260

<210> SEQ ID NO 5
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 5
atgccgcttg aaatgacgat tgctctcaac aatgtggtcg ccgtcgtcac cggcgcggcg      60
ggaggcatcg ccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga agttcgaaga cactccgctg     300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcggggtct gcgcggcgcg gcgttcaatg cggcctattg caccagcaag     480
gcggcggtga agatgctctc gaagtgcctc ggcgcggaat cgcggcgct cggctacaac     540 atccgcgtca actccgtgca tccgggcggc atcgataccc cgatgctcgg ctcggggatg     600
gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat tcgtgatgga cggcggcttc     780
```
agccaggtct ga                                                                 792

<210> SEQ ID NO 6
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 6

Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Gly Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260

<210> SEQ ID NO 7
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 7
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120

-continued

```
accgacatgg cgccctcggc cgatgtcgaa ggcgcggacc attatctcca gcacgacgtg    180
acgagcgagg ccggctggaa ggcggtcgcg gcgctggccc aggaaaagta cgggcgcgtc    240
gatgcgctgg tgcacaacgc gggcatctcg atcgtcacga agttcgaaga cactccgctg    300
tccgatttcc accgcgtgaa cacggtcaac gtcgattcca tcatcatcgg tacgcaggtc    360
ctgctgccgc tgctcaagga aggcggcaag gcgcgcgcag ggggcgcctc ggtggtcaac    420
ttctccagcg tcgggggtct gcgcggctcg gcgttcaatg cggcctattg caccagcaag    480
gcggcggtga agatgctctc gaagtgcctc ggcgcggaat cgcggcgct cggctacaac    540 atccgcgtca actccgtgca tccgggcggc atcgataccc cgatgctcgg ctcgatcatg    600
gacaagtacg tcgaactcgg cgctgccccc tcgcgcgagg tggcccaggc cgcgatggaa    660
atgcgccacc cgatcggtcg catgggtcgc cctgccgaaa tgggcggcgg cgtggtctat    720
ctctgctccg acgcagcaag cttcgtcacc tgcacggaat tcgtgatgga cggcggcttc    780
agccaggtct ga                                                        792
```

<210> SEQ ID NO 8
<211> LENGTH: 263
<212> TYPE: PRT
<213> ORGANISM: Artificial Sequence
<220> FEATURE:
<223> OTHER INFORMATION: Variant of ketoreductase from Novosphingobium aromaticivorans

<400> SEQUENCE: 8

```
Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ser Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Gly Val Val Tyr
```

```
                    225                 230                 235                 240
Leu Cys Ser Asp Ala Ala Ser Phe Val Thr Cys Thr Glu Phe Val Met
                245                 250                 255
Asp Gly Gly Phe Ser Gln Val
            260

<210> SEQ ID NO 9
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 9
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga gttcgaaga cactccgctg     300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgggggtct gcgcggcatt gcgttcaatg cggcctattg caccagcaag     480
gcggcggtga agatgctctc gaagtgcctc ggcgcggaat cgcggcgct cggctacaac     540
atccgcgtca actccgtgca tccgggcggc atcgataccc cgatgctcgg ctcgatcatg     600
gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat cgtgatgga cggcggcttc     780
agccaggtct ga                                                         792

<210> SEQ ID NO 10
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 10

Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110
```

```
Ser Ile Ile Ile Gly Thr Gln Val Leu Leu Pro Leu Leu Lys Glu Gly
            115                 120                 125

Gly Lys Ala Arg Ala Gly Ala Ser Val Val Asn Phe Ser Ser Val
        130                 135                 140

Gly Gly Leu Arg Gly Ile Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260
```

<210> SEQ ID NO 11
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 11

```
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga gttcgaaga cactccgctg      300 tccgatttcc accgcgtgaa cacggtcaac gtcgattcca tcatcatcgg tacgcaggtc     360
ctgctgccgc tgctcaagga aggcggcaag gcgcgcgcag gggcgcctc ggtggtcaac      420 ttctccagcg tcgggggct gcgcggctgg gcgttcaatg cggcctattg caccagcaag     480
gcggcggtga agatgctctc gaagtgcctc ggcgcggaat cgcggcgct cggctacaac      540 atccgcgtca actccgtgca tccgggcggc atcgataccc cgatgctcgg ctcgatcatg     600
gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat cgtgatgga cggcggcttc     780 agccaggtct ga                                                        792
```

<210> SEQ ID NO 12
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 12

Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65              70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Trp Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260

<210> SEQ ID NO 13
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 13
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgg tgcacaacgc gggcatctcg atcgtcacga gttcgaaga cactccgctg     300 tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgggggtct gcgcggcgcg gcgttcaatg cggcctattg caccagcaag     480

```
gcggcggtga agatgctctc gaagtgcctc ggcgcggaat tcgcggcgct cggctacaac      540
atccgcgtca actccgtgca tccgggcccg atcgataccc cgatgctcgg ctcgatcatg      600
gacaagtacg tcgaactcgg cgctgccccc tcgcgcgagg tggcccaggc cgcgatggaa      660
atgcgccacc cgatcggtcg catgggtcgc cctgccgaaa tgggcggcgg cgtggtctat      720
ctctgctccg acgcagcaag cttcgtcacc tgcacggaat tcgtgatgga cggcggcttc      780
agccaggtct ga                                                          792
```

<210> SEQ ID NO 14
<211> LENGTH: 263
<212> TYPE: PRT
<213> ORGANISM: Artificial Sequence
<220> FEATURE:
<223> OTHER INFORMATION: Variant of ketoreductase from Novosphingobium aromaticivorans

<400> SEQUENCE: 14

```
Met Pro Leu Glu Met Thr Ile Ala Leu Asn Asn Val Val Ala Val Val
 1               5                  10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Leu Ala Gln Glu Lys Tyr Gly Arg Val
 65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Pro Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260
```

<210> SEQ ID NO 15
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 15

| | |
|---|---:|
| atgccgcttg aaatgacgat tgctctcaac aatgtggtcg ccgtcgtcac cggcgcggcg | 60 |
| ggaggcatcg gccgcgaact ggtcaaggcg atgaaggccg ccaacgccat cgtcatcgcc | 120 |
| accgacatgg cgccctcggc cgatgtcgaa ggcgcggacc attatctcca gcacgacgtg | 180 |
| acgagcgagg ccggctggaa ggcggtcgcg gcgctggccc aggaaaagta cgggcgcgtc | 240 |
| gatgcgctgg tgcacaacgc gggcatctcg atcgtcacga agttcgaaga cactccgctg | 300 |
| tccgatttcc accgcgtgaa cacggtcaac gtcgattcca tcatcatcgg tacgcaggtc | 360 |
| ctgctgccgc tgctcaagga aggcggcaag gcgcgcgcag ggggcgcctc ggtggtcaac | 420 |
| ttctccagcg tcgggggtct gcgcggcgcg gcgttcaatg cggcctattg caccagcaag | 480 |
| gcggcggtga agatgctctc gaagtgcctc ggcgcggaat cgcggcgct cggctacaac | 540 |
| atccgcgtca actccgtgca tccgggccag atcgataccc cgatgctcgg ctcgatcatg | 600 |
| gacaagtacg tcgaactcgg cgctgccccc tcgcgcgagg tggcccaggc cgcgatggaa | 660 |
| atgcgccacc cgatcggtcg catgggtcgc cctgccgaaa tgggcggcgg cgtggtctat | 720 |
| ctctgctccg acgcagcaag cttcgtcacc tgcacggaat tcgtgatgga cggcggcttc | 780 |
| agccaggtct ga | 792 |

<210> SEQ ID NO 16
<211> LENGTH: 263
<212> TYPE: PRT
<213> ORGANISM: Artificial Sequence
<220> FEATURE:
<223> OTHER INFORMATION: Variant of ketoreductase from Novosphingobium
 aromaticivorans

<400> SEQUENCE: 16

Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gln Ile Asp

```
            180                 185                 190
Thr Pro Met Leu Gly Ser Ile Met Asp Lys Tyr Val Glu Leu Gly Ala
            195                 200                 205

Ala Pro Ser Arg Glu Val Ala Gln Ala Ala Met Glu Met Arg His Pro
        210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260

<210> SEQ ID NO 17
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 17
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
gatgcgctgt gcacaacgc gggcatctcg atcgtcacga agttcgaaga cactccgctg     300
tccgatttcc accgcgtgaa cacggtcaac gtcgattcca tcatcatcgg tacgcaggtc     360
ctgctgccgc tgctcaagga aggcggcaag gcgcgcgcag ggggcgcctc ggtggtcaac     420
ttctccagcg tcgggggtct gcgcggcgcg gcgttcaatg cggcctattg caccagcaag     480
gcggcggtga agatgctctc gaagtgcctc ggcgcggaat cgcggcgct cggctacaac     540 atccgcgtca actccgtgca tccgggcgtt atcgataccc cgatgctcgg ctcgatcatg     600
gacaagtacg tcgaactcgg cgctgccccc tcgcgcgagg tggcccaggc cgcgatggaa     660
atgcgccacc cgatcggtcg catgggtcgc cctgccgaaa tgggcggcgg cgtggtctat     720
ctctgctccg acgcagcaag cttcgtcacc tgcacggaat cgtgatgga cggcggcttc     780 agccaggtct ga                                                         792

<210> SEQ ID NO 18
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 18

Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60
```

```
Gly Trp Lys Ala Val Ala Leu Ala Gln Glu Lys Tyr Gly Arg Val
 65                  70                  75                  80

Asp Ala Leu Val His Asn Ala Gly Ile Ser Ile Val Thr Lys Phe Glu
                 85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Val Ile Asp
            180                 185                 190

Thr Pro Met Leu Gly Ser Ile Met Asp Lys Tyr Val Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260

<210> SEQ ID NO 19
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 19
atgccgcttg aaatgacgat tgctctcaac aatgtggtcg ccgtcgtcac cggcgcggcg     60
ggaggcatcg ccgcgaact ggtcaaggcg atgaaggccg ccaacgccat cgtcatcgcc    120
accgacatgg cgccctcggc cgatgtcgaa ggcgcggacc attatctcca gcacgacgtg    180
acgagcgagg ccggctggaa ggcggtcgcg cgctggccc aggaaaagta cgggcgcgtc    240
gatgcgctgg tgcacaacgc gggcatctcg atcgtcacga gttcgaaga cactccgctg    300 tccgatttcc accgcgtgaa cacggtcaac gtcgattcca tcatcatcgg tacgcaggtc    360
ctgctgccgc tgctcaagga aggcggcaag gcgcgcgcag ggggcgcctc ggtggtcaac    420
ttctccagcg tcgggggtct gcgcggcgcg gcgttcaatg cggcctattg caccagcaag    480
gcggcggtga agatgctctc gaagtgcctc ggcgcggaat cgcggcgct cggctacaac    540 atccgcgtca actccgtgca tccgggcggc atcgataccc cgatgctcgg ctcgatcatg    600
gacaagtact ttgaactcgg cgctgccccc tcgcgcgagg tggcccaggc cgcgatggaa    660
atgcgccacc cgatcggtcg catgggtcgc cctgccgaaa tgggcggcgg cgtggtctat    720
ctctgctccg acgcagcaag cttcgtcacc tgcacggaat tcgtgatgga cggcggcttc    780
agccaggtct ga                                                         792
```

```
<210> SEQ ID NO 20
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 20

Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Phe Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260

<210> SEQ ID NO 21
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 21
atgccgcttg aaatgacgat tgctctcaac aatgtggtcg ccgtcgtcac cggcgcggcg      60
ggaggcatcg gccgcgaact ggtcaaggcg atgaaggccg ccaacgccat cgtcatcgcc     120
accgacatgg cgccctcggc cgatgtcgaa ggcgcggacc attatctcca gcacgacgtg     180
acgagcgagg ccggctggaa ggcggtcgcg gcgctggccc aggaaaagta cgggcgcgtc     240
```

```
gatgcgctgg tgcacaacgc gggcatctcg atcgtcacga agttcgaaga cactccgctg    300
tccgatttcc accgcgtgaa cacggtcaac gtcgattcca tcatcatcgg tacgcaggtc    360
ctgctgccgc tgctcaagga aggcggcaag gcgcgcgcag ggggcgcctc ggtggtcaac    420
ttctccagcg tcgggggtct gcgcggcgcg gcgttcaatg cggcctattg caccagcaag    480
gcggcggtga agatgctctc gaagtgcctc ggcgcggaat cgcggcgct cggctacaac     540 atccgcgtca actccgtgca tccgggcggc atcgataccc cgatgctcgg ctcgatcatg    600
gacaagtact ttgaactcgg cgctgccccc tcgcgcgagg tggcccaggc cgcgatggaa    660
atgcgccacc cgatcggtcg catgggtcgc cctgccgaaa tgggcggcgg cgtggtctat    720
ctctgctccg acgcagcaag cttcgtcacc tgcacggaat tcgtgatgga cggcggcttc    780
agccaggtct ga                                                         792
```

<210> SEQ ID NO 22
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 22

```
Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val
    130                 135                 140

Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Gly Ile Asp
            180                 185                 190

Thr Pro Met Leu Gly Ser Ile Met Asp Lys Tyr Phe Glu Leu Gly Ala
        195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255
```

Asp Gly Gly Phe Ser Gln Val
            260

<210> SEQ ID NO 23
<211> LENGTH: 792
<212> TYPE: DNA
<213> ORGANISM: Artificial Sequence
<220> FEATURE:
<223> OTHER INFORMATION: Variant of ketoreductase from Novosphingobium
      aromaticivorans

<400> SEQUENCE: 23

| | | | | | |
|---|---|---|---|---|---|
| atgccgcttg | aaatgacgat | tgctctcaac | aatgtggtcg | ccgtcgtcac | cggcgcggcg | 60 |
| ggaggcatcg | gccgcgaact | ggtcaaggcg | atgaaggccg | ccaacgccat | cgtcatcgcc | 120 |
| accgacatgg | cgccctcggc | cgatgtcgaa | ggcgcggacc | attatctcca | gcacgacgtg | 180 |
| acgagcgagg | ccggctggaa | ggcggtcgcg | gcgctggccc | aggaaaagta | cgggcgcgtc | 240 |
| gatgcgctgg | tgcacaacgc | gggcatctcg | atcgtcacga | agttcgaaga | cactccgctg | 300 |
| tccgatttcc | accgcgtgaa | cacggtcaac | gtcgattcca | tcatcatcgg | tacgcaggtc | 360 |
| ctgctgccgc | tgctcaagga | aggcggcaag | gcgcgcgcag | ggggcgcctc | ggtggtcaac | 420 |
| ttctccagcg | tcggggggtct | gcgcggcgcg | gcgttcaatg | cggcctattg | caccagcaag | 480 |
| gcggcggtga | agatgctctc | gaagtgcctc | ggcgcggaat | cgcggcgct | cggctacaac | 540 |
| atccgcgtca | actccgtgca | tccgggcggc | atcgataccc | cgatgctcgg | ctcgatcatt | 600 |
| gacaagtacg | tcgaactcgg | cgctgccccc | tcgcgcgagg | tggcccaggc | cgcgatggaa | 660 |
| atgcgccacc | cgatcggtcg | catgggtcgc | cctgccgaaa | tgggcggcgg | cgtggtctat | 720 |
| ctctgctccg | acgcagcaag | cttcgtcacc | tgcacggaat | tcgtgatgga | cggcggcttc | 780 |
| agccaggtct | ga | | | | | 792 |

<210> SEQ ID NO 24
<211> LENGTH: 263
<212> TYPE: PRT
<213> ORGANISM: Artificial Sequence
<220> FEATURE:
<223> OTHER INFORMATION: Variant of ketoreductase from Novosphingobium
      aromaticivorans

<400> SEQUENCE: 24

Met Pro Leu Glu Met Thr Ile Ala Leu Asn Asn Val Val Ala Val Val
1               5                   10                  15

Thr Gly Ala Ala Gly Gly Ile Gly Arg Glu Leu Val Lys Ala Met Lys
            20                  25                  30

Ala Ala Asn Ala Ile Val Ile Ala Thr Asp Met Ala Pro Ser Ala Asp
        35                  40                  45

Val Glu Gly Ala Asp His Tyr Leu Gln His Asp Val Thr Ser Glu Ala
    50                  55                  60

Gly Trp Lys Ala Val Ala Ala Leu Ala Gln Glu Lys Tyr Gly Arg Val
65                  70                  75                  80

Asp Ala Leu Val His Asn Ala Gly Ile Ser Ile Val Thr Lys Phe Glu
                85                  90                  95

Asp Thr Pro Leu Ser Asp Phe His Arg Val Asn Thr Val Asn Val Asp
            100                 105                 110

Ser Ile Ile Ile Gly Thr Gln Val Leu Leu Pro Leu Leu Lys Glu Gly
        115                 120                 125

Gly Lys Ala Arg Ala Gly Gly Ala Ser Val Val Asn Phe Ser Ser Val

```
                130             135             140
Gly Gly Leu Arg Gly Ala Ala Phe Asn Ala Ala Tyr Cys Thr Ser Lys
145                 150                 155                 160

Ala Ala Val Lys Met Leu Ser Lys Cys Leu Gly Ala Glu Phe Ala Ala
                165                 170                 175

Leu Gly Tyr Asn Ile Arg Val Asn Ser Val His Pro Gly Ile Asp
            180                 185                 190

Thr Pro Met Leu Gly Ser Ile Ile Asp Lys Tyr Val Glu Leu Gly Ala
            195                 200                 205

Ala Pro Ser Arg Glu Val Ala Gln Ala Ala Met Glu Met Arg His Pro
    210                 215                 220

Ile Gly Arg Met Gly Arg Pro Ala Glu Met Gly Gly Val Val Tyr
225                 230                 235                 240

Leu Cys Ser Asp Ala Ala Ser Phe Val Thr Cys Thr Glu Phe Val Met
                245                 250                 255

Asp Gly Gly Phe Ser Gln Val
            260

<210> SEQ ID NO 25
<211> LENGTH: 1104
<212> TYPE: DNA
<213> ORGANISM: Geobacillus stearothermophilus

<400> SEQUENCE: 25
atggaattgt tcaaatatat ggaaacttac gattatgagc aagtgctgtt ttgccaagat      60
aaagaatcgg gtttgaaagc gatcattgcc attcatgaca caacgctcgg cccggcgctc     120
ggcgggacgc gcatgtggat gtacaattcg aagaagaag cgcttgaaga cgccttgcgc      180
ctcgcccgcg gcatgacgta caaaaacgcg gccgccggcc tcaacttggg cggggggcaaa    240 acggtcatca tcggcgaccc gcgcaaagat aaaaacgaag cgatgttccg ggcgttcggc     300
cgcttcattc aagggctgaa cggccgctac atcacggcgg aagacgtcgg cacgaccgtc     360
gccgatatgg atatcatcta tcaagaaacc gactatgtca ccggcatttc gcccgaattc     420
ggctcatccg caacccatc gccggcgacc gcctacggcg tataccgcgg catgaaggcg      480
gcggcaaaag aggcgttcgg cagcgattcg ctcgaaggaa agtcgtcgc cgtccaagga      540 gtcggcaatg tcgcgtatca tttgtgccgc catttgcacg aagaaggagc gaaactcatc    600
gtgactgaca tcaacaagga agtggtggcg cgcgcggtcg aggaattcgg agcgaaagcg    660
gtcgacccga cgacattta cggcgtggag tgcgacattt ttgctccatg cgcgctcggc    720
ggcatcatca cgatcaaac gattccgcaa ctgaaagcga agtgatcgc cggatcggcg      780 aacaaccagc tgaaagagcc gcgccatggc gacatcatcc atgaaatggg catcgtctat     840
gccccggatt atgtgatcaa cgccggcggc gtcatcaacg tcgcggacga actgtacggc     900
tacaatcggg aacgggcgat gaaaaaaatc gagcaaattt atgacaacat cgaaaagtg     960 tttgccatcg ccaagcgcga caacattcca acgtatgtgg ccgccgaccg gatggcggaa   1020
gaacggattg aaacgatgcg caaagcgcgc agtcaatttt tgcaaaatgg tcaccatatt   1080
ttaagccgcc gtcgcgcccg ctaa                                           1104

<210> SEQ ID NO 26
<211> LENGTH: 367
<212> TYPE: PRT
<213> ORGANISM: Geobacillus stearothermophilus

<400> SEQUENCE: 26
```

```
Met Glu Leu Phe Lys Tyr Met Glu Thr Tyr Asp Tyr Glu Gln Val Leu
1               5                   10                  15

Phe Cys Gln Asp Lys Glu Ser Gly Leu Lys Ala Ile Ile Ala Ile His
            20                  25                  30

Asp Thr Thr Leu Gly Pro Ala Leu Gly Gly Thr Arg Met Trp Met Tyr
                35                  40                  45

Asn Ser Glu Glu Glu Ala Leu Glu Asp Ala Leu Arg Leu Ala Arg Gly
            50                  55                  60

Met Thr Tyr Lys Asn Ala Ala Ala Gly Leu Asn Leu Gly Gly Lys
65                  70                  75                  80

Thr Val Ile Ile Gly Asp Pro Arg Lys Asp Lys Asn Glu Ala Met Phe
                85                  90                  95

Arg Ala Phe Gly Arg Phe Ile Gln Gly Leu Asn Gly Arg Tyr Ile Thr
            100                 105                 110

Ala Glu Asp Val Gly Thr Thr Val Ala Asp Met Asp Ile Ile Tyr Gln
            115                 120                 125

Glu Thr Asp Tyr Val Thr Gly Ile Ser Pro Glu Phe Gly Ser Ser Gly
130                 135                 140

Asn Pro Ser Pro Ala Thr Ala Tyr Gly Val Tyr Arg Gly Met Lys Ala
145                 150                 155                 160

Ala Ala Lys Glu Ala Phe Gly Ser Asp Ser Leu Glu Gly Lys Val Val
            165                 170                 175

Ala Val Gln Gly Val Gly Asn Val Ala Tyr His Leu Cys Arg His Leu
            180                 185                 190

His Glu Glu Gly Ala Lys Leu Ile Val Thr Asp Ile Asn Lys Glu Val
            195                 200                 205

Val Ala Arg Ala Val Glu Glu Phe Gly Ala Lys Ala Val Asp Pro Asn
210                 215                 220

Asp Ile Tyr Gly Val Glu Cys Asp Ile Phe Ala Pro Cys Ala Leu Gly
225                 230                 235                 240

Gly Ile Ile Asn Asp Gln Thr Ile Pro Gln Leu Lys Ala Lys Val Ile
            245                 250                 255

Ala Gly Ser Ala Asn Asn Gln Leu Lys Glu Pro Arg His Gly Asp Ile
            260                 265                 270

Ile His Glu Met Gly Ile Val Tyr Ala Pro Asp Tyr Val Ile Asn Ala
            275                 280                 285

Gly Gly Val Ile Asn Val Ala Asp Glu Leu Tyr Gly Tyr Asn Arg Glu
            290                 295                 300

Arg Ala Met Lys Lys Ile Glu Gln Ile Tyr Asp Asn Ile Glu Lys Val
305                 310                 315                 320

Phe Ala Ile Ala Lys Arg Asp Asn Ile Pro Thr Tyr Val Ala Ala Asp
            325                 330                 335

Arg Met Ala Glu Glu Arg Ile Glu Thr Met Arg Lys Ala Arg Ser Gln
            340                 345                 350

Phe Leu Gln Asn Gly His His Ile Leu Ser Arg Arg Arg Ala Arg
            355                 360                 365
```

PROCESSES USING AMINO ACID DEHYDROGENASES AND KETOREDUCTASE-BASED COFACTOR REGENERATING SYSTEM

The present application is a Divisional of U.S. patent application Ser. No. 15/184,242, filed Jun. 16, 2016, now U.S. Pat. No. 9,714,439, which is a Divisional of U.S. patent application Ser. No. 14/742,215, filed Jun. 17, 2015, now U.S. Pat. No. 9,394,551 which is a Divisional of U.S. patent application Ser. No. 13/577,772, filed Oct. 16, 2012, now U.S. Pat. No. 9,080,192 which is a national stage application filed under 35 USC § 371 and claims priority of the international application PCT/US2011/024102, filed Feb. 8, 2011, and U.S. provisional patent application 61/303,179, filed Feb. 10, 2010, each of which is hereby incorporated by reference herein.

TECHNICAL FIELD

The present disclosure relates to biocatalysts and processes for preparing chiral amino acids using the biocatalysts.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "CX2-038USP1_ST25.txt", a creation date of Feb. 9, 2010, and a size of 48 kilobytes. The sequence listing filed via EFS-Web is part of the specification and is hereby incorporated in its entirety by reference herein.

BACKGROUND

Amino acid dehydrogenases comprise a group of coenzyme-dependent enzymes that catalyze the reversible oxidative deamination of an amino acid to its keto acid and ammonia with the concomitant reduction of either cofactor NAD+, NADP+ or FAD. The enzyme with dehydrogenase properties is distributed in a number of diverse prokaryotic and eukaryotic organisms. Amino acid dehydrogenases have been studied widely because of their potential applications in biosensors or diagnostic kits, synthesis of L- and D-amino acids for use in production pharmaceutical peptides, herbicides and insecticides (Brunhuber et al., 1994, Crit. Rev. Biochem. Mol. Biol. 29(6):415-467; Hummel et al., 1989, Eur. J. Biochem. 184:1-13; Krix et al., 1997, J. Biotech. 53:29-39; Ohshima et al., 1990, Adv. Biochem. Eng. Biotechnol. 42:181-209; U.S. Pat. No. 7,550,277). For example, the anti-hypertensives ramipril, enalapril, benazapril, and prinivil are prepared using L-homophenylalanine, and certain second generation pril analogs are synthesized from p-substituted-L homophenylalanine. Certain β-lactam antibiotics use substituted D-phenylglycine side chains, and while other antibiotics are based on aminoadipic acid and other unnatural amino acids. The unnatural amino acids L-tert-leucine, L-nor-valine, L-nor-leucine, L-2-amino-5-[1,3]dioxolan-2yl-pentanoic acid have been used as a precursor in the synthesis of a number of different developmental drugs. The enzyme leucine dehydrogenase and mutants thereof have been shown to be capable of catalyzing the reductive amination of the corresponding 2-ketoacids of alkyl and branched-chain amino acids, and L-tert-leucine has been produced commercially with such an enzyme.

Given the industrial utility of L- and D-amino acid dehydrogenases, it is desirable to develop processes and systems that can enhance the biocatalytic reactions carried out by amino acid dehydrogenases.

SUMMARY

The present disclosure provides coupled systems for the efficient biosynthesis of chiral amino acid compounds using an L- or D-amino acid dehydrogenase ("AADH") coupled with a cofactor regenerating system comprising a ketoreductase ("KRED").

In certain embodiments, the present disclosure provides a process for converting a 2-oxo acid compound of formula I which is a substrate for an amino acid dehydrogenase to a chiral amino acid of formula IIa:

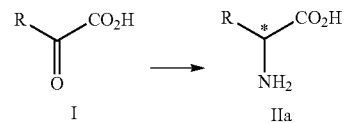

comprising contacting the compound of formula I with a reaction medium comprising an amino acid dehydrogenase, an ammonium ion donor, NAD+/NADH or NADP+/NADPH, and a cofactor regenerating system comprising a ketoreductase and a lower secondary alcohol, under conditions where the compound of formula I is converted to the chiral amino acid of formula IIa and the lower secondary alcohol is converted to a ketone. In certain embodiments of the process, R is a substituted or unsubstituted ($C_1$-$C_{10}$) alkyl, —($C_2$-$C_6$)alkenyl, —($C_2$-$C_6$)alkynyl, —($C_3$-$C_8$)cycloalkyl, heterocycloalkyl, aryl, or heteroaryl. In certain embodiments, R is a substituted or unsubstituted group selected from those groups shown in either of Table 1 or Table 2 disclosed herein.

In certain embodiments of the process for converting a compound of formula I which is a substrate for an amino acid dehydrogenase to a chiral amino acid of formula IIa, the amino acid dehydrogenase is an L-amino acid dehydrogenase and the chiral amino acid of formula IIa is IIb,

wherein the product of formula IIb is formed in enantiomeric excess. In certain embodiments, the L-amino acid dehydrogenase is from *Bacillus, Clostridium, Corynebacterium, Geobacillus, Natronobacterium, Synechocystis, Thermoactinomyces, Thermos, Thermomicrobium,* or *Carderia*. In some embodiments, the L-amino acid dehydrogenase is selected from L-alanine dehydrogenase, L-aspartate dehydrogenase, L-erythro-3,5-diaminohexanoate dehydrogenase, L-leucine dehydrogenase, L-glutamate dehydrogenase, lysine dehydrogenase, L-phenylalanine dehydrogenase, L-serine dehydrogenase, L-valine dehydrogenase, L-2,4-diaminopentanoate dehydrogenase, L-glutamate synthase, L-diaminopimelate dehydrogenase, L-N-methylalanine dehydrogenase, L-lysine 6-dehydrogenase, and L-tryptophan dehydrogenase.

In certain embodiments of the process for converting a compound of formula I which is a substrate for an amino acid dehydrogenase to a chiral amino acid of formula IIa, the amino acid dehydrogenase is a D-amino acid dehydrogenase and the chiral amino acid of formula IIa is IIc,

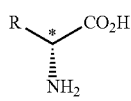

wherein the compound of formula IIc is formed in enantiomeric excess. In certain embodiments of the process, the D-amino acid dehydrogenase is from *Halobacterium, Methanosarcina, Pseudomonas, Pyrobaculum, Salmonella, Corynebacterium*, and *Escherichia*. In certain embodiments, the D-amino acid dehydrogenase is selected from a D-alanine dehydrogenase, D-threonine dehydrogenase, and D-proline dehydrogenase.

In certain embodiments of the process for converting a compound of formula I which is a substrate for an amino acid dehydrogenase to a chiral amino acid of formula IIa, the amino acid dehydrogenase comprises a L-leucine dehydrogenase, the compound of formula I is 3,3-dimethyl-2-oxobutanoic acid, the product of formula IIa is (S)-2-amino-3,3-dimethylbutanoic acid. In some embodiments of the process, the leucine dehydrogenase is a wild type leucine dehydrogenase or an engineered leucine dehydrogenase. In some embodiments, the leucine dehydrogenase is from *Bacillus, Clostridium, Corynebacterium, Geobacillus, Natronobacterium, Thermoactinomyces, Thermos, Thermomicrobium*, or *Carderia*. In some embodiments, the leucine dehydrogenase is from *Bacillus acidokaludarius, Bacillus brevis, Bacillus caldolyticus, Bacillus cereus, Bacillus megaterium, Bacillus mesentericus, Bacillus mycoides, Bacillus natto, Bacillus pumilus, Bacillus sp., Bacillus sphaericus, Bacillus stearothermophilus, Bacillus subtilis, Clostridium thermoaceticum, Corynebacterium pseudodiphtheriticum, Geobacillus stearothermophilus, Natronobacterium magadii*, or *Thermoactinomyces intermedius*. In some embodiments, the leucine dehydrogenase comprises the amino acid sequence of SEQ ID NO: 26.

In certain embodiments, the present disclosure provides a process for producing (S)-2-amino-3,3-dimethylbutanoic acid, comprising: contacting 3,3-dimethyl-2-oxobutanoic acid with a leucine dehydrogenase in a reaction medium comprising an ammonium ion donor, cofactor $NAD^+$/NADH or $NADP^+$/NADPH, and a cofactor recycling system comprising a ketoreductase and a lower secondary alcohol, under conditions where the 3,3-dimethyl-2-oxobutanoic acid is converted to (S)-2-amino-3,3-dimethylbutanoic acid, wherein the 3,3-dimethyl-2-oxobutanoic acid is at about 75 g/L to 125 g/L, the cofactor is at about 0.30 g/L to 0.70 g/L, and the leucine dehydrogenase and ketoreductase are each independently at about 0.5 to about 1.0 g/L. In certain embodiments of the process, the secondary alcohol is present in at least 1.5 fold stoichiometric excess of substrate. In some embodiments of the process, the secondary alcohol is isopropanol, wherein the isopropanol is at about 7% to 12% volume of the reaction medium by (weight/volume).

In certain embodiments, the present disclosure provides a process for converting a compound mixture of formula IId which comprises a substrate for an amino acid dehydrogenase to a composition of formula I and a chiral amino acid of formula IIa:

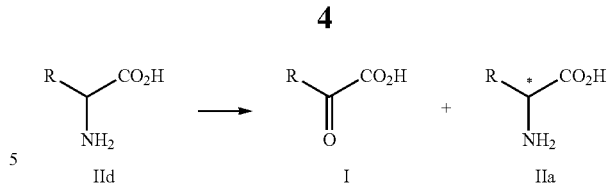

where the process comprises contacting the compound mixture of formula IId with an enantioselective amino acid dehydrogenase in a reaction medium comprising $NAD^+$/NADH or $NADP^+$/NADPH and a cofactor recycling system comprising a ketoreductase and a lower alkyl ketone, under conditions where the compound mixture of formula IId is converted to the composition of formula I and a chiral amino acid of formula IIa, and the lower alkyl ketone is converted to a lower secondary alcohol. In some embodiments of the process, the compound mixture of IId is a racemic mixture of formula IIe:

In some embodiments of the process, the amino acid dehydrogenase comprises an L-amino acid dehydrogenase and the chiral amino acid of formula IIa is IIc

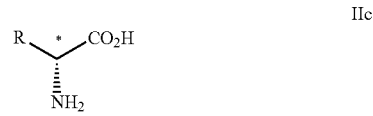

wherein the process results in chiral amino acid of formula IIc in enantiomeric excess. In some embodiments of the process, the amino acid dehydrogenase comprises a D-amino acid dehydrogenase and the chiral amino acid of formula IIa is IIb

wherein the process results in a chiral amino acid of formula IIb in enantiomeric excess.

In certain embodiments, the present disclosure provides a process for preparing an N-protected amino acid compound, wherein the method comprises: (i) contacting a compound of formula I with a reaction medium comprising an amino acid dehydrogenase, an ammonium ion donor, $NAD^+$/NADH or $NADP^+$/NADPH, and a cofactor regenerating system comprising a ketoreductase and a lower secondary alcohol under suitable conditions where the compound of formula I is converted to the chiral amino acid compound of formula IIa and the lower secondary alcohol is converted to a ketone; and (ii) contacting the amino acid compound of formula IIa with a compound comprising an N-protecting group under conditions, where the N-protecting group reacts with the compound of formula IIa to form an N-protected amino acid compound.

In certain embodiments of the process for preparing an N-protected amino acid compound, the biocatalytic step comprises contacting 3,3-dimethyl-2-oxobutanoic acid with a leucine dehydrogenase in a reaction medium comprising an ammonium ion donor, cofactor $NAD^+$/NADH or $NADP^+$/NADPH, and a cofactor recycling system comprising a ketoreductase and a lower secondary alcohol, under conditions where the 3,3-dimethyl-2-oxobutanoic acid is converted to (S)-2-amino-3,3-dimethylbutanoic acid. In some embodiments, the 3,3-dimethyl-2-oxobutanoic acid is at about 75 g/L to 125 g/L, the cofactor is at about 0.30 g/L to 0.70 g/L, and the leucine dehydrogenase and ketoreductase are each independently at about 0.5 to about 1.0 g/L. In some embodiments, the secondary alcohol is present in at least 1.5 fold stoichiometric excess of substrate. In some embodiments, the secondary alcohol is isopropanol, and the isopropanol is at about 7% to 12% volume of the reaction medium by (weight/volume). In some embodiments, the N-protecting group is selected from Cbz, FMOC, BOC and MOC.

In certain embodiments of the various processes for preparing chiral amino acid compounds disclosed herein, the process is carried out in a cell free system. In some embodiments of the various processes, the amino acid dehydrogenase is present as a crude extract, and in some embodiments, the amino acid dehydrogenase is substantially purified.

In certain embodiments of the various processes for preparing chiral amino acid compounds disclosed herein, the ketoreductase is a wild type ketoreductase or an engineered ketoreductase. In some embodiments, the ketoreductase is from *Lactobacillus, Candida, Novosphingobium,* or *Saccharomyces,* and in some embodiments, the ketoreductase is from an organism selected from *Lactobacillus kefir, Lactobacillus brevis, Lactobacillus minor, Candida magnoliae, Saccharomyces cerevisiae,* and *Novosphingobium aromaticivorans.* In some embodiments, the ketoreductase is an engineered ketoreductase derived from the wild-type ketoreductase of *Novosphingobium aromaticivorans,* wherein the engineered ketoreductase comprising an amino acid sequence having at least 80%, 85%, 90%, 95%, 98%, 99%, or more identity to a sequence selected from SEQ ID NO: 2, 4, 6, 8, 10, 12, 14, 16, 18, 20, 22, and 24.

In certain embodiments of the various processes for preparing chiral amino acid compounds disclosed herein, the ketoreductase is characterized by increased thermostability, increased solvent stability, and/or increased enzymatic activity relative to a reference ketoreductase. In some embodiments, the ketoreductase used in the cofactor recycling system has an improved property over a reference ketoreductase of increased activity in the conversion of the lower secondary alcohol (e.g., isopropanol) of the recycling system to the corresponding lower alkyl ketone. In some embodiments, the ketoreductase having the increased activity in the conversion of the lower secondary alcohol is at least 2.0 fold, 2.5 fold, 5.0 fold, 7.5 fold, 10-fold, or more improved relative to a reference ketoreductase (e.g., a reference ketoreductase of SEQ ID NO: 2).

In certain embodiments of the various processes for preparing chiral amino acid compounds disclosed herein, the ketoreductase used in the cofactor recycling system has an improved property over a reference ketoreductase of decreased or no activity with the compound of formula I (e.g., trimethylpyruvic acid) which is a substrate for the amino acid dehydrogenase used in the process. In some embodiments of the process, the activity of the ketoreductase used in the cofactor recycling system with the compound of formula I is less than about 5%, 2%, 1%, 0.5%, 0.1%, 0.05%, 0.01%, or an even smaller %, of the activity of the amino acid dehydrogenase used in the process with the compound of formula I. In some embodiments of the process, the ketoreductase used in the cofactor recycling system has no activity with the compound of formula I.

In certain embodiments of the various processes for preparing chiral amino acid compounds disclosed herein, the ketoreductase used in the cofactor recycling system is an engineered ketoreductase is capable of recycling cofactor by converting isopropanol (IPA) to acetone in a reaction medium of 3 to 20% IPA at a pH of about 9.0 to 10.5 with an activity at least 1.5-fold greater than the reference ketoreductase of SEQ ID NO: 2.

In certain embodiments of the various processes for preparing chiral amino acid compounds disclosed herein, the process further comprises removing from the reaction medium the ketone formed from the lower secondary alcohol, and in certain embodiments the lower secondary alcohol is isopropanol and the ketone removed is acetone. In some embodiments, the secondary alcohol is present in at least 1.5 fold stoichiometric excess of substrate.

In certain embodiments of the various processes for preparing chiral amino acid compounds disclosed herein, the reaction medium is at a pH of about 8.5 to about 10.5, or a pH of about 8.5 to about 9.5, or a pH of about 9.0.

In certain embodiments of the various processes for preparing chiral amino acid compounds disclosed herein, the reaction medium is at a temperature of about 25° C. to about 45° C., or about 35° C. to about 40° C.

DETAILED DESCRIPTION

Definitions

As used herein, the following terms are intended to have the following meanings.

"Protein," "polypeptide," "oligopeptide," and "peptide" are used interchangeably to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Amino acid dehydrogenase" or "AADH" are used interchangeably herein to refer to a polypeptide capable of carrying out the conversion of an amino acid, in the presence of an electron acceptor, to a 2-oxo acid, $NH_3$, and reduced acceptor. In some embodiments, amino acid dehydrogenases are also capable of carrying out the reverse reaction of converting the 2-oxo acid, in the presence of an ammonium ion donor and an electron donor, to an amino acid and oxidized electron donor. L-amino acid dehydrogenase refers to an amino acid dehydrogenase that is stereospecific or stereoselective for an L-amino acid. D-amino acid dehydrogenase refers to an amino acid dehydrogenase that is stereospecific or stereoselective for a D-amino acid. Generally, the electron acceptor/donor for the amino acid dehydrogenase is nicotinamide adenine dinucleotide in oxidized/reduced form (i.e., NAD+/NADH) or nicotinamide adenine dinucleotide phosphate in oxidized/reduced form (i.e., NADP+/NADPH). Amino acid dehydrogenase as used herein include naturally occurring (wild type) amino acid dehydrogenases as well as non-naturally occurring polypeptides generated by human manipulation (e.g., recombinant or engineered enzymes).

"Ketoreductase" and "KRED" are used interchangeably herein to refer to a polypeptide that is capable of reducing a ketone to an alcohol product and/or oxidizing an alcohol to a ketone product. The polypeptide typically utilizes a cofactor reduced nicotinamide adenine dinucleotide (NADH) or reduced nicotinamide adenine dinucleotide phosphate (NADPH) as the reducing agent; or may use the corresponding $NAD^+$ or $NADPH^+$ as oxidizing agent. Ketoreductases as used herein include naturally occurring (wild type) ketoreductases as well as non-naturally occurring polypeptides generated by human manipulation (e.g., recombinant or engineered enzymes). They may be used to effect one or more chemical transformations, including the regeneration of cofactors such as NAD(P)H or $NAD(P)^+$.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Recombinant" or "engineered" or "non-naturally occurring" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques (e.g., genetic engineering). Non-limiting examples include, among others, recombinant cells expressing genes that are not found within the native (non-recombinant) form of the cell or express native genes that are otherwise expressed at a different level.

"Derived from" identifies the originating polypeptide, and/or the gene encoding such polypeptide, upon which the engineering was based.

"Substrate" refers to a substance or compound that is converted or meant to be converted into another compound by the action of an enzyme. The term includes aromatic and aliphatic compounds, and includes not only a single compound, but also combinations of compounds, such as solutions, mixtures and other materials which contain at least one substrate.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly reported in the art (typically as a percentage) as the enantiomeric excess calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in the sum with others.

"Stereospecific" refers to the preferential conversion in a chemical or enzymatic reaction of one stereoisomer over another. Stereospecificity can be partial, where the conversion of one stereoisomer is favored over the other, or it may be complete where only one stereoisomer is converted.

"Increased enzymatic activity" refers to an improved property of an enzyme, which can be represented by an increase in specific activity (e.g., product produced/time/weight protein) or an increase in percent conversion of the substrate to the product (e.g., percent conversion of starting amount of substrate to product in a specified time period using a specified amount of KRED) as compared to a reference enzyme. Exemplary methods to determine enzyme activity are provided in the Examples. Any property relating to enzyme activity may be affected, including the classical enzyme properties of Km, Vmax or kcat, changes of which can lead to increased enzymatic activity. Improvements in enzyme activity can be from about 1.5 times the enzymatic activity of the corresponding wild-type ketoreductase enzyme, to as much as 2 times. 5 times, 10 times, 20 times, 25 times, 50 times, 75 times, 100 times, or more enzymatic activity than the naturally occurring ketoreductase or another engineered ketoreductase from which the ketoreductase polypeptides were derived. In specific embodiments, the engineered enzyme exhibits improved enzymatic activity in the range of 1.5 to 50 times, 1.5 to 100 times greater than that of the parent enzyme. It is understood by the skilled artisan that the activity of any enzyme is diffusion limited such that the catalytic turnover rate cannot exceed the diffusion rate of the substrate, including any required cofactors. The theoretical maximum of the diffusion limit, or kcat/Km, is generally about $10^8$ to $10^9$ (M−1 s−1). Hence, any improvements in the enzyme activity of an enzyme will have an upper limit related to the diffusion rate of the substrates acted on by the enzyme. Comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells to minimize variations in amount of enzyme produced by the host cells and present in the lysates.

"Conversion" refers to the enzymatic transformation of the substrate to the corresponding product. "Percent conversion" refers to the percent of the substrate that is converted to the product within a period of time under specified conditions. Thus, the "enzymatic activity" or "activity" of an enzyme(s) can be expressed as "percent conversion" of the substrate to the product.

"Improved thermostability" and "improved thermal stability" are used interchangeably herein to refer to a property of increased resistance to inactivation when exposed to a set temperature or set of temperatures in defined conditions as compared to the resistance to inactivation of a reference enzyme. Activity of the enzyme pre- and post treatment are measured under the same defined assay condition. Thermostability can also be compared and expressed as the temperature at which half of the initial activity is retained after a defined incubation time after an increase from one temperature to another, i.e., from X° C. to Y° C. "Residual activity" or "residual enzyme activity" refers to the activity that remains following exposure to the set temperature in a defined condition.

"Solvent stable" refers to a polypeptide that maintains similar activity (more than e.g., 60% to 80%) after exposure to varying concentrations (e.g., 5-99%) of solvent (isopropyl alcohol, tetrahydrofuran, 2-methyltetrahydrofuran, acetone, toluene, butylacetate, methyl tert-butylether, etc.) for a period of time (e.g., 0.5-24 hrs) compared to the untreated polypeptide.

"pH stable" refers to a polypeptide that maintains similar activity (more than e.g., 60% to 80%) after exposure to high or low pH (e.g., 4.5-6 or 8 to 12) for a period of time (e.g., 0.5-24 hrs) compared to the untreated polypeptide.

"Thermo- and solvent stable" refers to a polypeptide that is both thermostable and solvent stable, particularly with respect to its biological function, e.g., enzymatic activity.

"Cofactor" refers a substance that is necessary or beneficial to the activity of an enzyme. In the context of an amino acid dehydrogenase, the cofactor is generally a nicotinamide cofactor. "Nicotinamide cofactor" refers to any type of the oxidized and reduced forms of nicotinamide adenine dinucleotide (NAD+ and NADH, respectively) and the oxidized and reduced forms of nicotinamide adenine dinucleotide phosphate (NADP+ and NADPH, respectively) and derivatives and analogs thereof. With regard to a nicotinamide cofactor, the term "derivative" means any compound containing a pyridine structural element, including nicotinamides that have been chemically modified by attachment to soluble or insoluble polymeric materials. Some examples of derivatives of nicotinamide cofactors are described in U.S. Pat. No. 5,106,740, and Mansson and Mosbach, 1987, Methods in Enzymology 136:3 45, the disclosures of which are incorporated herein by reference. The term "analogs," as used herein, refers to materials that undergo a formal hydride transfer in a redox reaction similar to that undergone by nicotinamide cofactors. Examples of analogs of nicotinamide cofactors useful in the practice of the present process include compounds described in U.S. Pat. No. 5,801,006, the disclosure of which is incorporated herein by reference. Other suitable cofactors, as defined herein, can be used in the practice of the invention, as would be recognized by those skilled in the art.

"Cofactor regenerating system" and "cofactor recycling system" are used interchangeably herein to refer to a set of reactants that participate in a reaction that reduces the oxidized form of the cofactor (e.g., NADP+ to NADPH). In the embodiments herein, cofactors oxidized by the amino acid dehydrogenase-catalyzed reaction are regenerated in reduced form by the cofactor regenerating system. Cofactor regenerating systems comprise a stoichiometric reductant that is a source of reducing hydrogen equivalents and is capable of reducing the oxidized form of the cofactor. The cofactor regenerating system may further comprise a catalyst, for example an enzyme catalyst, that catalyzes the reduction of the oxidized form of the cofactor by the reductant.

"Alkyl" by itself or as part of another substituent refers to a saturated branched or straight hydrocarbon chain derived by the removal of one hydrogen atom from a single carbon atom of a parent alkane. Alkyl groups include, but are not limited to, methyl; ethyl; propyls, such as propan-1-yl, propan-2-yl (isopropyl), etc.; butyls, such as butan-1-yl, butan-2-yl (sec-butyl), 2-methyl propan-1-yl (isobutyl), 2-methyl propan-2-yl (t-butyl), etc.; and the like. In some embodiments, the alkyl groups are ($C_1$-$C_6$) alkyl. "Lower alkyl" refers to a straight-chain or branched saturated aliphatic hydrocarbon having 1 to 6, preferably 1 to 4, carbon atoms. Typical lower alkyl groups include methyl, ethyl, propyl, isopropyl, butyl, t-butyl, 2-butyl, pentyl, hexyl and the like.

"Alkenyl" refers to by itself or as part of another substituent refers to an unsaturated branched, straight chain or cyclic alkyl having at least one carbon-carbon double bond derived by the removal of one hydrogen atom from a single carbon atom of a parent alkene. The group may be in either the cis or trans conformation about the double bond(s). Alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In some embodiments, the alkenyl group is ($C_2$-$C_6$) alkenyl.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In some embodiments, the alkynyl group is (C2-C6) alkynyl.

"Heteroalkyl," Heteroalkanyl," Heteroalkenyl," Heteroalkynyl," Heteroalkyldiyl" and "Heteroalkyleno" by themselves or as part of another substituent refer to alkyl, alkanyl, alkenyl, alkynyl, alkyldiyl and alkyleno groups, respectively, in which one or more of the carbon atoms are each independently replaced with the same or different heteroatoms or heteroatomic groups. Heteroatoms and/or heteroatomic groups which can replace the carbon atoms include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen or ($C_1$-$C_6$) alkyl.

"Cycloalkyl" and "Heterocycloalkyl" by themselves or as part of another substituent refer to cyclic versions of "alkyl" and "heteroalkyl" groups, respectively. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

"Aryl" by itself or as part of another substituent refers to a monovalent aromatic hydrocarbon group having the stated number of carbon atoms (i.e., $C_5$-$C_{15}$ means from 5 to 15 carbon atoms) derived by the removal of one hydrogen atom from a single carbon atom of a parent aromatic ring system. Aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In some embodiments, the aryl group is ($C_5$-$C_{15}$) aryl, with ($C_5$-$C_{10}$) being even more preferred. In some embodiments, the aryls are cyclopentadienyl, phenyl and naphthyl.

"Heteroaryl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrone, benzothiadiazole, benzothiazole, benzotriazole, benzoxazine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof. In some embodiments, the heteroaryl group is a 5-14 membered heteroaryl. In some embodiments, the heteroaryl group is a 5-10 membered heteroaryl.

"Substituted" when used to modify a specified group or radical, means that one or more hydrogen atoms of the specified group or radical are each, independently of one another, replaced with the same or different substituent(s). Each substituent can be the same or different. Examples of suitable substituents include, but are not limited to, alkyl, alkenyl, alkynyl, cycloalkyl, aryl, aralkyl, cycloheteroalkyl, heteroaryl, $OR^a$ (e.g., hydroxyl, alkoxy (e.g., methoxy, ethoxy, and propoxy), aryloxy, heteroaryloxy, aralkyloxy, ether, ester, carbamate, etc.), hydroxyalkyl, alkoxycarbonyl, alkoxyalkoxy, perhaloalkyl, perfluoroalkyl (e.g., $CF_3$, $CF_2$, $CF_3$), perfluoroalkoxy (e.g., $OCF_3$, $OCF_2CF_3$), alkoxyalkyl, $SR^a$ (e.g., thiol, alkylthio, arylthio, heteroarylthio, aralkylthio, etc.), $S^+R^a{}_2$, $S(O)R^a$, $SO_2R^a$, $NR^aR^a$ (e.g., primary amine (i.e., $NH_2$), secondary amine, tertiary amine, amide, carbamate, urea, etc.), hydrazide, halide, nitrile, nitro, sulfide, sulfoxide, sulfone, sulfonamide, thiol, carboxy, aldehyde, keto, carboxylic acid, ester, amide, imine, and imide, including seleno and thio derivatives thereof, wherein each of the substituents can be optionally further substituted. In embodiments in which a functional group with an aromatic carbon ring is substituted, such substitutions will typically number less than about 10 substitutions, more preferably about 1 to 5, with about 1 or 2 substitutions being preferred.

"Amino acid" refers to a molecule having the general formula $NHR^b$—$CHR^{b'}$—COOH (wherein R is H, and $R^{b'}$ is an amino acid side chain, or R and $R^{b'}$ together with the carbon and nitrogen to which they are bonded form a ring, e.g., proline) which is capable of forming a peptide bond with one or more other molecules having the same general formula. The term embraces both L and D amino acids. A "chiral amino acid" refers to an amino acid in which the α-carbon is an asymmetric carbon atom, which is a carbon atom bonded to four different entities, such that an interchanging of any two groups gives rise to an enantiomer. In the context of an amino acid, a chiral amino acid of general formula NHR—CHR'—COOH, the R' group is an amino acid side chain other than H. A chiral amino acid can be an L-amino acid or a D-amino acid.

"Alcohol" refers to an alkyl group in which one or more of the hydrogen atoms has been replaced by an —OH group. A "lower alcohol" refers to an alcohol in which the alkyl group is about 1 to about 6 carbon atoms. A "secondary alcohol" refers to an alcohol in which the —OH group is bonded to a carbon atom that is bonded to one hydrogen atom and to two other carbon atoms, such as in 2-propanol (isopropanol), 2-butanol, 2-hexanol and the like. A "lower secondary alcohol" refers to a secondary alcohol in which the alkyl group is of 3 to about 6 carbon atoms.

"Ketone" refers to a carbonyl compound of general formula R'—C(O)—R" in which the carbonyl carbon is bonded to two carbon atoms. In some embodiments, R' and R" are the same and in some embodiments, R' and R" are each independently an optionally substituted alkyl or aryl. A lower alkyl ketone refers to a carbonyl compound of general formula R'—C(O)—R" in which R' and R" is each an alkyl of $C_1$ to $C_5$ carbon atoms, where the total number of carbon atoms in the ketone is 3 to 6 carbon atoms.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in P. G. M. Wuts and T. W. Greene, "Greene's Protective Groups in Organic Synthesis—Fourth Edition," John Wiley and Sons, New York, N.Y., 2007, Chapter 7 ("Greene") which chapter is hereby incorporated by reference in its entirety, and Harrison et al., *Compendium of Synthetic Organic Methods*, Vols. 1-8, 1971-1996, John Wiley & Sons, NY.

"N-protecting group" (or nitrogen protecting group) means a substituent commonly employed to block or protect a nitrogen functionality (e.g., the amine nitrogen of an amino acid) while carrying out a reaction with other functional groups on a compound. Accordingly, an "N-protected" compound refers to a modified form of the compound where an N-protecting group is blocking a nitrogen functionality on the compound from undergoing reaction.

"Ammonium source" or "ammonium ion donor" refers to a compound or composition that forms ammonia or ammonium ion in a reaction medium.

"Reaction medium" refers to a solution comprising a mixture of two or more components (e.g., enzyme, substrate, cofactor) which can undergo reaction in the solution. For the enzymatic reactions described herein the reaction medium typically is an at least partially aqueous solution. In some embodiments, the reaction medium comprises aqueous and organic solvents (e.g., isopropanol), one or more phases.

"Isolated polypeptide" refers to a polypeptide which is separated from other contaminants that naturally accompany it, e.g., protein, lipids, and polynucleotides. The term embraces polypeptides which have been removed or purified from their naturally-occurring environment or expression system (e.g., host cell or in vitro synthesis).

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure ketoreductase composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species.

Processes Using Amino Acid Dehydrogenases Coupled to Ketoreductase-Based Cofactor Regenerating System The present disclosure provides a process for the conversion of a 2-oxo acid (i.e., a keto acid) to an amino acid in the presence of an ammonium source in a reaction mediated by an amino acid dehydrogenase ("AADH") and a cofactor recycling system comprising a ketoreductase ("KRED"), as generally depicted in Scheme 1.

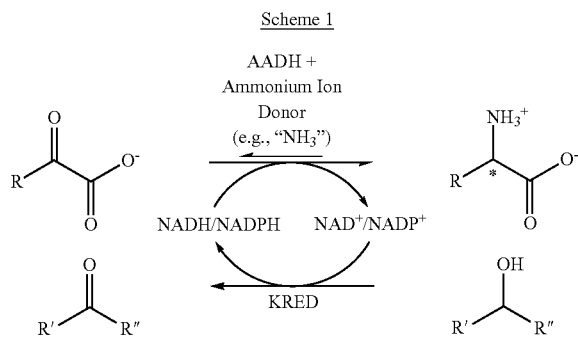

Scheme 1

The stereoselectivity of the amino acid dehydrogenase can be exploited to carry out the reverse reaction, i.e., conversion of an amino acid to the 2-oxo acid, and permit chiral resolution of L- and D-amino acids.

In the conversion of the 2-oxo acid to the amino acid, amino acid dehydrogenases typically use a cofactor, generally nicotinamide adenine dinucleotide (NAD+/NADH) or nicotinamide adenine dinucleotide phosphate (NADP+/NADPH). To enhance the amino acid dehydrogenase-mediated process, a cofactor regenerating system of formate dehydrogenase, glucose dehydrogenase, or phosphite dehydrogenase have been used to convert the oxidized NAD+/NADP+ to the reduced form NADH/NADPH. See, e.g., US patent publication 2009087995; US patent publication 20090117627; EP1925674; Johannes et al., 2005, Appl Environ Microbiol. 71(10):5728-5734; Johannes et al., 2007, Biotechnol Bioeng. 96(1):18-26; McLachan et al., 2008, Biotechnol Bioeng. 99(2):268-274). By continual replenishment of the reduced NADH or NADPH, the equilibrium of the amino acid dehydrogenase mediated process can be shifted towards product formation, thereby increasing the conversion of the oxo acid to the amino acid product. A whole cell-based system for conversion of D-amino acid to L-amino acid using amino oxidase, amino acid dehydrogenase, and a cofactor regenerating system is described in U.S. Pat. No. 7,217,544. The patent publication describes the use of formate dehydrogenase, malate dehydrogenase or alcohol dehydrogenase activities present in whole cells for regeneration of the cofactor. A coupled enzyme system of a phenylalanine dehydrogenase and a cofactor regenerating system using an alcohol dehydrogenase is described in Paradisi et al., 2007, J. Biotech. 128:408-411. However, in Paradisi et al., ethanol was employed as the substrate for the alcohol dehydrogenase, thereby forming acetaldehyde as the product.

As provided in the present disclosure, it has been found that processes using amino acid dehydrogenases when carried out in the presence of a cofactor regenerating system comprising a ketoreductase and an alcohol can be used for the efficient conversion of an oxo acid to its corresponding amino acid. In particular, use of a lower secondary alcohol for the ketoreductase-based cofactor regenerating system can increase the conversion of oxo acid to the amino acid in the amino acid dehydrogenase catalyzed reaction, avoiding the production of acetaldehyde which can react with and inactivate enzymes. Moreover, the ketone product formed by the ketoreductase catalyzed reaction, such as acetone, is less volatile than acetaldehyde, thereby providing greater control over the reaction, particularly in larger scale processes (e.g., reaction medium of 50 L, 100 L, 300 L, 500 L, or even greater volume).

Further, the loss of process control due to the volatility of acetaldehyde would create greater difficulty when using an amino acid dehydrogenase in the reverse reaction (e.g., converting amino acid to the corresponding oxo acid) as described in greater detail herein. In particular, pushing the equilibrium of the reverse reaction would be facilitated with a less volatile lower alkyl ketone such as acetone.

Although advantageously less volatile than acetaldehyde, the ketone product formed by the ketoreductase reaction of a lower secondary alcohol (e.g., acetone) is sufficiently volatile to allow its facile removal from the reaction medium thereby shifting the equilibrium of the ketoreductase mediated process towards further cofactor reduction, and further conversion of oxo acid to the amino acid by the amino acid dehydrogenase. Consequently, the combination of a ketoreductase and lower secondary alcohol provides the advantages greater reaction control (and increased safety) and enhanced ability to drive the desired amino acid dehydrogenase reaction to completion.

Significant benefit can be further obtained when engineered ketoreductases that have improved enzyme properties, including among others, increased enzymatic activity, increased thermostability, increased solvent stability and/or increased pH stability are used in the process. Engineered ketoreductases with such improved properties can allow use of conditions not well tolerated by the naturally occurring enzymes, including conditions such as, for example, high oxo acid concentration, high alcohol concentration, high ammonium ion donor concentration, elevated incubation temperatures, and increased incubation times. Use of engineered ketoreductases also can reduce the amount of enzyme needed in the process.

Accordingly, the present disclosure provides a process for converting a 2-oxo acid compound of formula I that is a substrate for an amino acid dehydrogenase to a chiral amino acid compound of formula IIa,

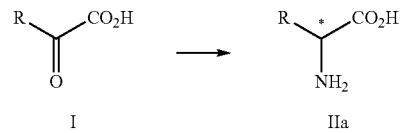

in a reaction medium comprising NAD+/NADH or NADP+/NADPH, and a cofactor regenerating system, where the cofactor regenerating system comprises a ketoreductase and a secondary alcohol. In particular, the secondary alcohol is a lower secondary alcohol, such as isopropanol, 2-butanol, 3-methyl-2-butanol, 2-pentanol, 3-pentanol, or 3,3-dimethyl-2-butanol.

In some embodiments, the process comprises contacting the 2-oxo acid compound of formula I with a reaction medium comprising an amino acid dehydrogenase, an ammonium ion donor, NAD+/NADH or NADP+/NADPH, and a cofactor regenerating system comprising a ketoreductase and a lower secondary alcohol, under suitable conditions where the compound of formula I is converted to the chiral amino acid compound of formula IIa and the lower secondary alcohol is converted to a ketone.

In the processes herein, the 2-oxo acid compound of formula I is a substrate for the amino acid dehydrogenase. Accordingly, the R group in the compound of formula I can be a substituted or unsubstituted: $(C_1-C_{10})$alkyl, —$(C_2-C_6)$alkenyl, —$(C_2-C_6)$alkynyl, heteroalkyl, —$(C_3-C_8)$cycloalkyl, heterocycloalkyl, aryl, or heteroaryl. Since amino acid dehydrogenases are known to recognize naturally occurring amino acids, the R group can be any side chain attached to the alpha carbon of an amino acid of a naturally occurring amino acid. These include, among others, the following side chain structures shown in Table 1 (where squiggly line denotes point of connection of R group to rest of molecule):

TABLE 1

![Table 1 structures]

Other R groups recognized by amino acid dehydrogenases include, among others, the following structures shown in Table 2 (where squiggly line denotes point of connection of R group to rest of molecule):

TABLE 2

![Table 2 structure]

TABLE 2-continued

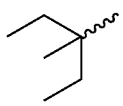

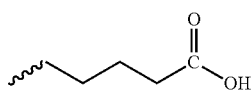

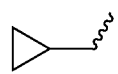

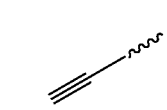

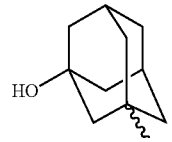

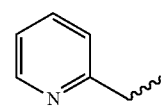

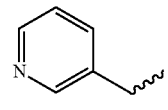

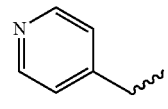

TABLE 2-continued

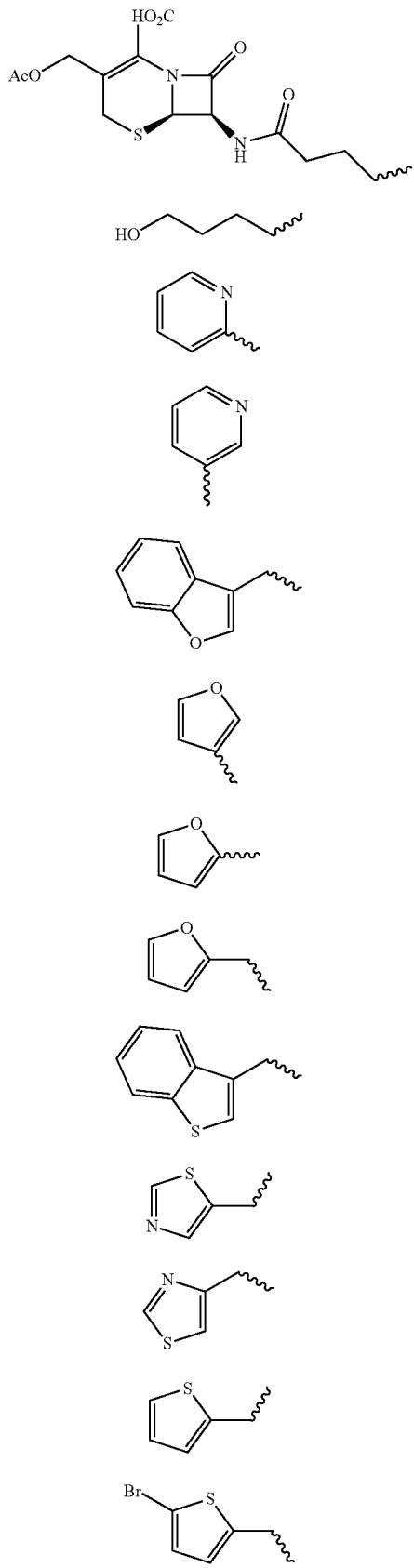

TABLE 2-continued

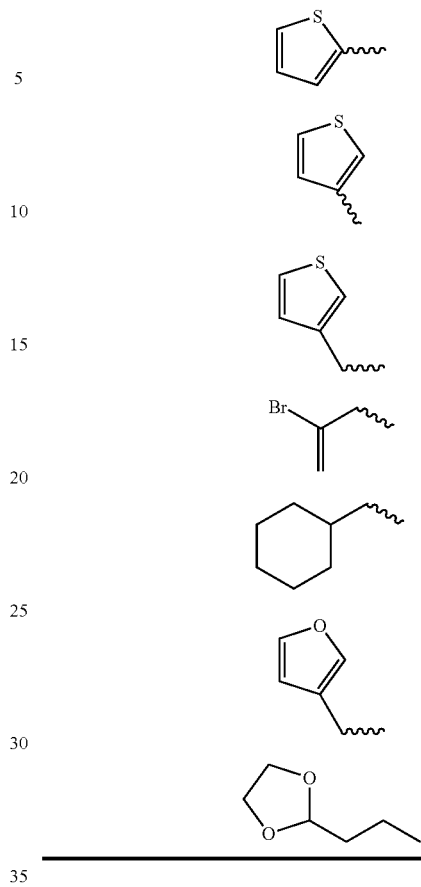

In some embodiments, the amino acid dehydrogenase can be an L- or D-amino acid dehydrogenase. In other words, in the process for conversion of a pro-chiral 2-oxo acid of formula I to the amino acid of formula IIa, the amino acid dehydrogenase can be enantioselective for the L- or D-amino acid. Thus, by selection of the appropriate amino acid dehydrogenase, the process of the present disclosure can be used to produce the L- or D-amino acid in enantiomeric excess from the prochiral 2-oxo acid. The amino acid dehydrogenase can be a naturally occurring, i.e., wild type, amino acid dehydrogenase or an engineered amino acid dehydrogenase. The engineered amino acid dehydrogenase can be selected for improved properties, such as increased enzymatic activity, thermostability, solvent stability, pH stability, co-factor preference, and/or altered substrate specificity.

In some embodiments of the process, the amino acid dehydrogenase comprises a L-amino acid dehydrogenase and the chiral amino acid compound of formula IIa is IIb, IIb

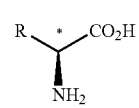

having the indicated chirality. In this process, the chiral amino acid of formula IIb is formed in enantiomeric excess. In some embodiments, the chiral amino acid of formula IIb can be formed in at least 25%, 50%, 55%, 60%, 65%, 70%, 75%, 80%, 85%, 90%, 95%, 96%, 97%, 98%, or 99% or more in enantiomeric excess. In some embodiments, the chiral amino acid of formula IIb is formed in greater than 99% enantiomeric excess.

Various L-amino acid dehydrogenase can be obtained from organisms of the genus *Bacillus, Clostridium, Corynebacterium, Geobacillus, Natronobacterium, Synechocystis, Thermoactinomyces, Thermomicrobium, Carderia, Citrobacter, Proteus,* and *Pseudomonas,* as well as from mammalian sources (e.g., beef liver). Specific organisms where the L-amino acid dehydrogenase can be obtained include, among others, *Bacillus subtilis, Bacillus sphaericus, Bacillus stearothermophilus, Bacillus thermoproteoliticus, Brevibacterium* sp., *Clostridium symbiosum, Clostridium difficile, Geobacillus stearothermophilus, Natronobacterium magadii, Synechocystis* sp. PCC 6803, *Thermoactinomyces intermedius, Citrobacter* sp., *Proteus* sp., and *Pseudomonas* sp.

L-amino acid dehydrogenases useful in the process of the present disclosure capable of carrying out the conversion of an L-amino acid, in the presence of an electron acceptor, to a 2-oxo acid, $NH_3$, and reduced acceptor. Suitable L-amino acid dehydrogenases have been described in e.g., Oshima et al., International Industrial Biotechnology 9 (1989) 5-11; Ohsima et al., European Journal of Biochemistry 191 (1990) 715-720; Khan et al., Bioscience, Biotechnology and Biochemistry 69 (2005) 1861-1870; Hummel et al., Applied Microbiology and Biotechnology 26 (1987) 409-416 and Bommarius in Enzyme Catalysis in Organic Synthesis, 2nd Edition (2002), ed. Drauz and Waldmann, Wiley-VCH Weinheim.

The polynucleotide and/or amino acid sequences of various L-amino acid dehydrogenases are known in the art and are available from known public databases e.g., the GenBank (located at www.ncbi.nlm.nih.gov). In some embodiments, L-enantioselective amino acid dehydrogenases useful with the process of the present disclosure have been described with respect to the type of amino acid acted upon/formed in the enzyme catalyzed process. Accordingly, in some embodiments, useful L-amino acid dehydrogenase references and sequence information can be obtained by entering into the indexed and searchable public databases any one of the following enzyme classifications: L-alanine dehydrogenase (EC 1.4.1.1) (see e.g., Ohashima et al., 1979, Eur J Biochem. 100(1):29-30; Grimshaw et al., 1981, Biochemistry. September 29; 20(20):5650-5), L-aspartate dehydrogenase (EC 1.4.1.21), L-erythro-3,5-diaminohexanoate dehydrogenase (EC 1.4.1.11), L-leucine dehydrogenase (EC 1.4.1.9), L-glutamate dehydrogenase (EC 1.4.1.2), glutamate dehydrogenase (NAD(P)+) (EC 1.4.1.3), glutamate dehydrogenase (NADP+) (EC 1.4.1.4), glycine dehydrogenase (EC 1.4.1.10), lysine dehydrogenase (EC 1.4.1.15), L-phenylalanine dehydrogenase (EC 1.4.1.20), L-serine dehydrogenase (EC 1.4.1.7), L-valine dehydrogenase (EC 1.4.1.8), L-2,4-diaminopentanoate dehydrogenase, L-glutamate synthase, L-diaminopimelate dehydrogenase (EC 1.4.1.12), L-N-methylalanine dehydrogenase, L-lysine 6-dehydrogenase, and L-tryptophan dehydrogenase, glutamate synthase (NADPH) (EC 1.4.1.13); glutamate synthase (NADH>) (EC 1.4.1.14), diaminopimelate dehydrogenase (EC 1.4.1.16); N-methylalanine dehydrogenase (EC 1.4.1.17), lysine 6-dehydrogenase (EC 1.4.1.18), and tryptophan dehydrogenase (EC 1.4.1.19). The choice of the amino acid dehydrogenase can be based on the type of oxo acid substrate recognized by the enzyme.

In some embodiments, the L-amino acid dehydrogenases are engineered L-amino acid dehydrogenases in which mutations have been introduced into the naturally occurring polypeptide to generate an enzyme with altered properties. Engineered L-amino acid dehydrogenases are described for, by way of example and not limitation, L-phenylalanine dehydrogenase (see e.g., Seah et al., 1995 FEBS Lett. 370(1-2):93-96; Busca et al., 2004, Org. Biomol. Chem. 2, 2684-2691.)

In some embodiments, the amino acid dehydrogenase comprises a D-amino acid dehydrogenase, and the chiral amino acid of formula IIa is IIc,

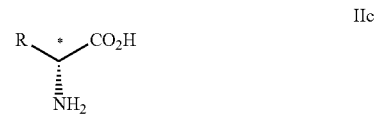

having the indicated chirality. In this process, the chiral amino acid of formula IIc is formed in enantiomeric excess. In some embodiments, the chiral amino acid of formula IIc can be formed in at least 25%, 50%, 55%, 60%, 65%, 70%, 75%, 80%, 85%, 90%, 95%, 96%, 97%, 98%, or 99% or more in enantiomeric excess. In some embodiments, the chiral amino acid of formula IIc is formed in greater than 99% enantiomeric excess.

D-amino acid dehydrogenases can be obtained from *Halobacterium, Methanosarcina, Pseudomonas, Pyrobaculum, Salmonella, Corynebacterium,* and *Escherichia.* Specific species where the D-amino acid dehydrogenase can be obtained include, among others, *Pseudomonas aeruginosa, Pseudomonas fluorescens, Pyrobaculum islandicum, Salmonella typhimurium, Corynebacterium glutamicum,* and *Escherichia coli.*

Like the L-amino acid dehydrogenases, references and sequences of wild-type D-amino acid dehydrogenases are publicly available, for example from the GenBank database available at the NCBI web-site. A few exemplary wild-type D-amino acid dehydrogenase sequences listed by GenBank accession include: AAC36880 D-amino acid dehydrogenase [*Escherichia coli*] gi|145703|gb|AAC36880.1|[145703]; AAC36881 catabolic alanine racemase [*Escherichia coli*] gi|145704|gb|AAC36881.1|[145704]; AAC38139 D-amino acid dehydrogenase [*Klebsiella aerogenes*] gi|2360965|gb|AAC38139.1|[2360965]; AAC74273 D-amino acid dehydrogenase [*Escherichia coli* str. K-12 substr. MG1655] gi|1787438|gb|AAC74273.1|[1787438]; AAD06449 D-Amino acid dehydrogenase [*Helicobacter pylori* J99] gi|4155445|gb|AAD06449.1|[4155445]; AAF40633 D-amino acid dehydrogenase, small subunit [*Neisseria meningitidis* MC58] gi|7225395|gnl|tigr|NMB0176|gb|AAF40633.1|[7225395]; AAF83661 D-amino acid dehydrogenase subunit [*Xylella fastidiosa* 9a5c] gi|9105759|gb|AAF83661.1|AE003925_1 [9105759]; AAF93951 D-amino acid dehydrogenase, small subunit [*Vibrio cholerae* O1 biovar El Tor str. N16961] gi|9655235|gb|AAF93951.1||gnl|TIGR|VC0786[9655235]; AAF95141 2,4-dienoyl-CoA reductase [*Vibrio cholerae* O1 biovar El Tor str. N16961] gi|9656535|gb|AAF95141.1||gnl|TIGR|VC1993[9656535]; AAG08469 probable oxidoreductase [*Pseudomonas aeruginosa* PAO1] gi|9951378|gb|AAG08469. 1|AE004921_6|gnl|PseudoCAP|PA5084[9951378]; AAG08689 D-amino acid dehydrogenase, small subunit [*Pseudomonas aeruginosa* PAO1] gi|9951620|gb|AAG08689. 1|AE004943_5|gnl|PseudoCAP|PA5304[9951620]; AAG56040 D-amino acid dehydrogenase subunit [*Escherichia coli* O157:H7 EDL933] gi|12514889|gb|AAG56040.1|AE005336_1[12514889];

AAK90026 D-amino acid dehydrogenase [*Agrobacterium tumefaciens* str. C58] gi|15159999|gb|AAK90026.1| [15159999]; AAK90097 D-amino acid dehydrogenase, small subunit [*Agrobacterium tumefaciens* str. C58] gi|15160086|gb|AAK90097.1|[15160086]; AAL20718 D-amino acid dehydrogenase subunit [*Salmonella enterica* subsp. *enterica* serovar *Typhimurium* str. LT2] gi|16420334|gb|AAL20718.1|[16420334]; AAL53615 d-amino acid dehydrogenase small subunit [*Brucella melitensis* bv. 1 str. 16M] gi|117984529|gb|AAL53615.1||gnl|integgen|BMEII0373 [17984529]; AAL73201 putative D-amino acid dehydrogenase [*Agrobacterium* sp. IP I-671] gi|18478564|gb|AAL73201.1|AF335479_5[18478564]; AAM38531 D-amino acid dehydrogenase subunit [*Xanthomonas axonopodis* pv. *citri* str. 306] gi|21110075|gb|AAM38531.1||gnl|unicamp|XAC3688 [21110075]; AAM42918 D-amino acid dehydrogenase subunit [*Xanthomonas campestris* pv. *campestris* str. ATCC 33913] gi|21114929|gb|AAM42918.1||gnl|unicamp|XCC3648 [21114929]; AAM85736 D-amino acid dehydrogenase subunit [*Yersinia pestis* KIM 10] gi|21959016|gb|AAM85736.1|AE013821_2[21959016]; AAN34096 D-alanine dehydrogenase, small subunit [*Brucella suis* 1330] gi|23464296|gnl|tigr|BRA0924|gb|AAN34096.1| [23464296]; AAN42793 D-amino acid dehydrogenase subunit [*Shigella flexneri* 2a str. 301] gi|56383395|gb|AAN42793.2||gnl|mgcchina|SF0001178 [56383395]; and AAN69891 D-amino acid dehydrogenase, small subunit, putative [*Pseudomonas putida* KT2440] gi|24986030|gb|AAN69891.1|AE016628_4|gnl|tigr|PP4311 [24986030]. In some embodiments, the D-amino acid dehydrogenase is selected from D-alanine dehydrogenase (e.g., gi|23464296|gb|AAN34096.1| D-alanine dehydrogenase, small subunit [*Brucella suis* 1330]), D-threonine dehydrogenase (e.g., gi|3845577|dbj|BAA34184.1|D-threonine dehydrogenase [*Pseudomonas cruciviae*]), D-proline dehydrogenase (e.g., gi|45283977|gb|ABP51559.1|D-proline dehydrogenase [*Pyrobaculum arsenaticum* DSM 13514]).

In some embodiments, the D-amino acid dehydrogenases are engineered D-amino acid dehydrogenases in which mutations have been introduced into the naturally occurring polypeptide to generate an enzyme with altered enzyme properties. Engineered D-amino acid dehydrogenases are described in e.g., Vedha-Peters et al., "Creation of a Broad-Range and Highly Stereoselective D-Amino Acid Dehydrogenase for the One-Step Synthesis of D-Amino Acids" J. Am. Chem. Soc. 2006, 128, 10923-10929, or in U.S. Pat. No. 7,550,277, which is hereby incorporated by reference herein.

In the process mediated by the amino acid dehydrogenases, the reaction medium contains an ammonium source, which provides the $NH_3$ group for formation of the amino acid of formula IIa from the 2-oxo acid of formula I. Any compound which is suitable for this purpose can be used as the ammonium source. Exemplary compounds include, among others, ammonium salts, such as ammonium halide (e.g., ammonium chloride), ammonium formate, ammonium sulfate, ammonium phosphate, ammonium nitrate, ammonium tartrate, and ammonium acetate.

While the process described herein is generally used for the preparation of L- or D-amino acids, the amino acid dehydrogenase can also carry out the reverse reaction, i.e., conversion of an amino acid to its corresponding 2-oxo acid. When the substrate is an enantiomerically pure L- or D-amino acid, an appropriate amino acid dehydrogenase can be used for the conversion of the amino acid to the 2-oxo acid. For instance, an L-amino acid dehydrogenase is selected for conversion of L-amino acid preparations to the corresponding 2-oxo acid.

In some embodiments, the stereospecificity of amino acid dehydrogenases can be exploited for the chiral resolution of mixtures of L- and D-amino acids. For example, an L-amino acid dehydrogenase can be used to stereospecifically convert the L-amino acid in a mixture of L- and D-amino acids to the corresponding 2-oxo acid, thereby resulting in a composition that has the D-amino acid in enantiomeric excess. Similarly, a D-amino acid dehydrogenase can be used to stereospecifically convert the D-amino acid in a mixture of L- and D-amino acids to the corresponding 2-oxo acid, thereby resulting in a composition that has the L-amino acid in enantiomeric excess. When desired, the amino acid present in enantiomeric excess can be isolated from the product mixture.

Accordingly, in some embodiments, the present disclosure provides a process for converting a compound mixture of formula IId, which comprises a substrate for an amino acid dehydrogenase, to a composition of a 2 oxo acid compound of formula I and a chiral amino acid of formula IIa:

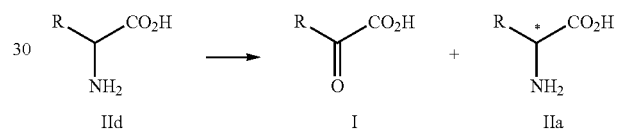

having a chiral carbon marked with an *, where the compound mixture of formula IId comprises L- and D-amino acid compounds of formula IIb and IIc and the chiral amino acid of formula IIa is an L- or D-amino acid. In these embodiments, the process for chiral resolution of a mixture of L- and D-amino acids can comprise contacting the compound mixture of formula IId with a reaction medium comprising an enantioselective amino acid dehydrogenase, $NAD^+/NADH$ or $NADP^+/NADPH$, and a cofactor recycling system comprising a ketoreductase and a lower alkyl ketone, under conditions where either the L-amino acid or D-amino acid of the compound mixture of formula IId is converted to a compound of formula I thereby resulting in an enantiomeric excess of the amino acid of formula IIa (which the chiral amino acid not converted by the amino acid dehydrogenase), and the lower alkyl ketone is converted to a lower secondary alcohol.

In some embodiments of the process, the compound mixture of IId is a racemic mixture of L- and D-amino acid compounds of formulas IIb and IIc, as represented by formula IIe:

In some embodiments, the process can be used for the chiral resolution of a mixture of L- and D-amino acids to form a chiral amino acid of formula IIc:

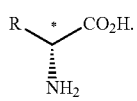

IIc having the indicated chirality in enantiomeric excess. In these embodiments, the process can comprise contacting the compound mixture of formula IId (which can include a racemic mixture of formula IIe) with a reaction medium comprising an L-amino acid dehydrogenase, NAD$^+$/NADH or NADP$^+$/NADPH and a cofactor recycling system comprising a ketoreductase and a lower alkyl ketone, under conditions where the chiral amino acid compound of formula IIb in the compound mixture of formula IId is converted to the 2-oxo acid compound of formula I thereby resulting in an enantiomeric excess of the chiral amino acid of formula IIc, and the lower alkyl ketone is converted to the corresponding lower secondary alcohol. In some embodiments, the chiral amino acid of formula IIc can be formed in at least 25%, 50%, 55%, 60%, 65%, 70%, 75%, 80%, 85%, 90%, 95%, 96%, 97%, 98%, or 99% or more in enantiomeric excess. In some embodiments, the chiral amino acid of formula IIc is formed in greater than 99% enantiomeric excess.

In the process for chiral resolution of a mixture of L- and D-amino acids to form the D-amino acid in enantiomeric excess, the L-amino acid dehydrogenase can be from *Bacillus, Clostridium, Corynebacterium, Geobacillus, Natronobacterium, Synechocystis, Thermoactinomyces, Thermos, Thermomicrobium,* or *Carderia*.

In some embodiments, the L-amino acid dehydrogenase can be selected from L-alanine dehydrogenase, L-aspartate dehydrogenase, L-erythro-3,5-diaminohexanoate dehydrogenase, L-leucine dehydrogenase, L-glutamate dehydrogenase, lysine dehydrogenase, L-phenylalanine dehydrogenase, L-serine dehydrogenase. L-valine dehydrogenase, L-2,4-diaminopentanoate dehydrogenase, L-glutamate synthase, L-diaminopimelate dehydrogenase, L-N-methylalanine dehydrogenase, L-lysine 6-dehydrogenase, and L-tryptophan dehydrogenase, as described above.

In some embodiments, the process can be used for the chiral resolution of a mixture of L- and D-amino acids to form the chiral amino acid of formula IIb,

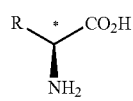

IIb having the indicated chirality in enantiomeric excess. In these embodiments, the process can comprise contacting the compound mixture of formula IId (which can include a racemic mixture of formula IIe) with a reaction medium comprising a D-amino acid dehydrogenase, NAD$^+$/NADH or NADP$^+$/NADPH and a cofactor recycling system comprising a ketoreductase and a lower alkyl ketone, under conditions where the chiral amino acid of formula IIc in the compound mixture of formula IId is converted to the 2-oxo acid compound of formula I thereby resulting in an enantiomeric excess of the chiral amino acid of formula IIb, and the lower alkyl ketone is converted to the corresponding lower secondary alcohol. In some embodiments, the chiral amino acid of formula IIb can be formed in at least 25%, 50%, 55%, 60%, 65%, 70%, 75%, 80%, 85%, 90%, 95%, 96%, 97%, 98%, or 99% or more in enantiomeric excess. In some embodiments, the chiral amino acid of formula IIb is formed in greater than 99% enantiomeric excess.

In the process for chiral resolution of a mixture of L- and D-amino acids to form the L-amino acid in enantiomeric excess, the D-amino acid dehydrogenase can be from *Halobacterium, Methanosarcina, Pseudomonas, Pyrobaculum, Salmonella, Corynebacterium,* or *Escherichia*.

In some embodiments of the process herein, the amino acid dehydrogenase can be present in the form of whole cells, including whole cells transformed with polynucleotide constructs expressing wild type or engineered amino acid dehydrogenases. In some embodiments, the amino acid dehydrogenase can be present in the form of cell extracts and/or lysates thereof, and may be employed in a variety of different forms, including solid (e.g., lyophilized, spray-dried, and the like) or semisolid (e.g., a crude paste). In some embodiments, the amino acid dehydrogenase is isolated, and can be in a substantially purified form. In some embodiments of the process, both the amino acid dehydrogenase and the ketoreductase of the regenerating system can be present in the form of whole cells, including whole cells transformed with polynucleotide constructs such that the whole cells express both the amino acid dehydrogenase and the ketoreductase.

In the embodiments of the processes disclosure herein, the amino acid dehydrogenase is used in combination with cofactor regenerating system comprising: a ketoreductase capable of reducing NAD$^+$ and/or NADP$^+$ to NADH and NADPH, respectively, and an alcohol (e.g., a lower secondary alcohol) that is a substrate for the ketoreductase. In the reduction of the cofactor, the ketoreductase converts the alcohol to the corresponding carbonyl compound (e.g., a lower alkyl ketone).

In the embodiments herein, the ketoreductase can be a wild type ketoreductase, or an engineered ketoreductase, in particular an engineered ketoreductase with an improved enzyme property. As used herein, a ketoreductase enzyme that has an "improved enzyme property" refers to a ketoreductase enzyme that exhibits an improvement in any enzyme property as compared to a reference ketoreductase enzyme. For the engineered ketoreductase enzymes described herein, the comparison is generally made to the wild-type ketoreductase enzyme, although in some embodiments, the reference ketoreductase can be an improved engineered ketoreductase. In some embodiments, the ketoreductase is an engineered ketoreductase characterized by increased thermostability, increased solvent stability, increased pH stability, and/or increased enzymatic activity relative to the wild type ketoreductase.

In some embodiments of the process, the ketoreductase used in the cofactor recycling system has an improved property over a reference ketoreductase of increased activity in the conversion of the lower secondary alcohol (e.g., isopropanol) of the recycling system to the corresponding lower alkyl ketone. In some embodiments, the ketoreductase having the increased activity in the conversion of the lower secondary alcohol is at least 2.0 fold, 2.5 fold, 5.0 fold, 7.5 fold, 10-fold, or more improved relative to a reference ketoreductase. In some embodiments, the ketoreductase is an engineered ketoreductase derived from the wild-type ketoreductase of *Novosphingobium aromaticivorans* (e.g., gi|145322460|gb|ABP64403.1|[145322460]).

The improved activity of engineered ketoreductases (derived from *Novosphingobium aromaticivorans* ketoreductase of SEQ ID NO: 2) for the conversion of the secondary alcohol, isopropanol (IPA) to its corresponding product, acetone was determined relative to the same activity for the reference ketoreductase of SEQ ID NO: 2. Relative IPA activity was determined using an assay with the following reaction conditions: 100 μl 10× diluted engineered KRED lysate, 10% IPA (v/v), 0.5 g/L NAD+, 100 mM TEA, pH 7.5. Exemplary engineered ketoreductases exhibiting at least 2-fold increased activity with IPA relative to SEQ ID NO: 2 are listed in Table 3. The fold-improvement in IPA activity relative to SEQ ID NO: 2 was quantified as follows: "+" indicates at least 200% to 250% improvement; "++" indicates <250% to 500% improvement; and "+++" indicates >500% to 1000% improvement; and "++++" indicates >1000% to 2000% improvement.

TABLE 3

| SEQ ID NO: | FIOP in IPA activity |
|---|---|
| 2 | [control] |
| 4 | + |
| 6 | ++ |
| 8 | ++ |
| 10 | ++ |
| 12 | +++ |
| 14 | ++ |
| 16 | + |
| 18 | ++++ |
| 20 | ++ |
| 24 | +++ |

In some embodiments, the ketoreductase having the increased activity in the conversion of the lower secondary alcohol is an engineered ketoreductase comprising an amino acid sequence having at least 80%, 85%, 90%, 95%, 98%, 99%, or more identity to a sequence selected from SEQ ID NO: 2, 4, 6, 8, 10, 12, 14, 16, 18, 20, 22, and 24. In some embodiments, the ketoreductase having the increased activity in the conversion of the lower secondary alcohol is an engineered ketoreductase comprising an amino acid sequence selected from SEQ ID NO: 4, 6, 8, 10, 12, 14, 16, 18, 20, 22, and 24.

In some embodiments of the process, the ketoreductase used in the cofactor recycling system has an improved property over a reference ketoreductase of decreased or no activity with the 2-oxo acid compound of formula I (e.g., trimethylpyruvic acid) which is a substrate for the amino acid dehydrogenase used in the process. In some embodiments of the process, the activity of the ketoreductase used in the cofactor recycling system with the compound of formula I is less than about 5%, 2%, 1%, 0.5%, 0.1%, 0.05%, 0.01%, or an even smaller percentage of the activity of the amino acid dehydrogenase used in the process with the compound of formula I. In some embodiments of the process, the ketoreductase used in the cofactor recycling system has no detectable activity with the 2-oxo acid compound of formula I.

The relative IPA activity of each of the engineered ketoreductases shown in Table 3 was measured under the same conditions in the presence of the compound of formula I, trimethylpyruvic acid (10% IPA (v/v), 0.5 g/L NAD+, 1 mM TMP, 100 mM TEA pH 7.5, 100 μl 10×KRED diluted lysate). Less than 5% increase or decrease was seen in the presence of the TMP, indicating that the engineered ketoreductases listed in Table 3 did not use TMP as a substrate.

Various ketoreductases that can be used in the cofactor regenerating system include ketoreductases from, by way of example and not limitation, bacteria, such as the genus *Escherichia*, the genus *Bacillus*, the genus *Pseudomonas*, the genus *Serratia*, the genus *Brevibacterium*, the genus *Corynebacterium*, the genus *Streptococcus*, the genus *Lactobacillus*, the genus *Novosphingobium*; actinomycetes such as the genus *Rhodococcus*, the genus *Streptomyces*; yeasts such as the genus *Saccharomyces*, the genus *Kluyveromyces*, the genus *Thermoanerobium*, the genus *Schizosaccharomyces*, the genus *Sporobolomyces*, the genus *Zygosaccharomyces*, the genus *Yarrowia*, the genus *Trichosporon*, the genus *Rhodosporidium*, the genus *Pichia*, the genus *Candida*; and fungi such as the genus *Neurospora*, the genus *Aspergillus*, the genus *Cephalosporium*, the genus *Trichoderma*.

In some embodiments, the ketoreductase can be derived from *Lactobacillus kefir*, *Lactobacillus brevis*, *Lactobacillus minor*, *Candida sonorensis*, *Candida boidini*, *Candida guilliermondi*, *Candida magnoliae*, *Candida utilis*, *Candida maltosa*, *Candida kefir*, *Candida parapslosis*, *Geotrichum candidum*, *Rhodococcus erythropolis*, *Rhodotorula glutinis*, *Hansenula fabianii*, *Hansenula polymorpha*, *Hansenula saturnus*, *Nocardia salmonicolor*, *Novosphingobium aromaticivorans*, *Pichia anomala*, *Pichia capsulata*, *Pichia membranafaciens*, *Pichia methanolica*, *Pichia pinus*, *Pichia silvicola*, *Pichia stipitis*, *Sphingomonas paucimobilis*, *Sporobolomyces salmonicolor*, *Streptomyces coelicolor*, *Thermoanerobium brockii*, or *Saccharomyces cerevisiae*.

In some embodiments, the ketoreductase is a wild-type ketoreductase listed in Table 4 or an engineered ketoreductase derived from a wild-type ketoreductase listed in Table 4.

TABLE 4

| Wild type KRED from various microorganisms | | | |
|---|---|---|---|
| Microorganism | Genbank Acc. No. | GI No. | Reference |
| *Candida magnoliae* | AB036927.1 | 12657576 | SEQ ID No 2 in US publ. no. 20060195947A1 |
| *Saccharomyces cerevisiae* | NP_010159.1 | 6320079 | SEQ ID NO: 110 in US publ. no. 20090191605A1 |
| *Lactobacillus brevis* | 1NXQ_A | 30749782 | SEQ ID NO: 2 in US publ. no. 20090191605A1 |
| *Rhodococcus erythropolis* | AAN73270.1 | 34776951 | SEQ ID NO: 112 in US publ. no. 20090191605A1 |
| *Saccharomyces cerevisiae* | NP_011476 | 6321399 | SEQ ID NO: 114 in US publ. no. 20090191605A1 |
| *Saccharomyces cerevisiae* | NP_010656.1 | 6320576 | SEQ ID NO: 116 in US publ. no. 20090191605A1 |
| *Saccharomyces cerevisiae* | NP_014490.1 | 6324421 | SEQ ID NO: 118 in US publ. no. 20090191605A1 |

TABLE 4-continued

Wild type KRED from various microorganisms

| Microorganism | Genbank Acc. No. | GI No. | Reference |
|---|---|---|---|
| Lactobacillus kefir | AAP94029.1 | 33112056 | SEQ ID NO: 4 in US publ. no. 20090191605A1 |
| Sporobolomyces salmonicolor | Q9UUN9 | 30315955 | SEQ ID No 104 in US publ. no. 20090191605A1 |
| Streptomyces coelicolor | NP_631415.1 | 21225636 | SEQ ID No 102 in US publ. no. 20090191605A1 |
| Thermoanaerobium brockii | X64841.1 | 1771790 | SEQ ID No 108 in US publ. no. 20090191605A1 |
| Candida parapsilosis | BAA24528 | 2815409 | Julich Chiral Solutions Cat. No. 03.11 |
| Lactobacillus brevis | ABJ63353.1 | 116098204 | Julich Chiral Solutions Cat. No. 8.1 |
| Candida boidinii | CAD66648 | 28400789 | Julich Chiral Solutions Cat. No. 02.10 |
| Lactobacillus leichmannii | | | Fluka Cat. No. 61306 |

In some embodiments, the ketoreductase is from *Lactobacillus*, such as, among others, *Lactobacillus kefir*, *Lactobacillus brevis*, or *Lactobacillus minor*. Wild type ketoreductase from *Lactobacillus kefir* is described in Genbank accession no. AAP94029 GI:33112056. Wild type ketoreductase from *Lactobacillus brevis* is described in CAD66648 GI:28400789.

In some embodiments, the ketoreductase is an engineered ketoreductase derived from a wild type ketoreductase of *Lactobacillus*. Engineered ketoreductases of *Lactobacillus*, for example, *L. kefir*, *L. brevis*, and *L. minor*, with improved enzyme properties are described in US patent publications US20080318295, US20090093031, US20090191605, US20090155863, US20090162909, U.S. Ser. No. 12/545,034, filed Aug. 20, 2009, U.S. Ser. No. 12/545,761, filed Aug. 21, 2009, U.S. Ser. No. 12/549,154, filed Aug. 27, 2009, and U.S. Ser. No. 12/549,293, filed Aug. 27, 2009, of which each of the ketoreductase polypeptides disclosed therein are hereby incorporated by reference herein.

In some embodiments, the ketoreductase of *Candida* is from *Candida magnoliae*. Wild type ketoreductase of *Candida magnoliae* is described in e.g., Wada et al., *Biosci. Biotechnol. Biochem.* 62(2): 280-285 (1998). Engineered ketoreductases with improved enzyme properties derived from *Candida magnoliae* ketoreductase is described in US20060195947, of which each of the ketoreductase polypeptides disclosed therein is hereby incorporated by reference herein.

In some embodiments, the ketoreductase of *Saccharomyces* is from *Saccharomyces cerevisiae*. Wild type ketoreductase from *Saccharomyces cerevisiae* is described in US20080248539. Engineered ketoreductases with improved enzyme properties derived from *Saccharomyces cerevisiae* ketoreductase are described in US20080248539. Each of the ketoreductase polypeptides disclosed therein are incorporated by reference herein.

In some embodiments, the ketoreductase of *Novosphingobium* is from *Novosphingobium aromaticivorans*. A wild type ketoreductase gene from *Novosphingobium aromaticivorans* is provided as GenBank accession CP000677.1, and the encoded polypeptide sequence is accession no. gi|145322460|gb|ABP64403.1|[145322460]. Engineered ketoreductases derived from *Novosphingobium aromaticivorans* wild type are described in U.S. provisional application 61/219,162, filed Jun. 22, 2009, which is hereby incorporated by reference herein. Exemplary engineered polynucleotides and the corresponding ketoreductase polypeptides derived from the *Novosphingobium aromaticivorans* wild type and having the improved property of increased activity in converting isopropanol to acetone are presented in the sequence listing incorporated herein as SEQ ID NO: 3-24. In some embodiments, the engineered ketoreductase comprises an amino acid sequence selected from the group consisting of SEQ ID NO: 4, 6, 8, 10, 12, 14, 16, 18, 20, 22, and 24.

In some embodiments, the ketoreductase used in the process is capable of recycling cofactor by converting isopropanol (IPA) to acetone in a reaction medium of 3 to 20% IPA at a pH of about 9.0 to 10.5 with an activity at least 1.5-fold greater than the reference ketoreductase of SEQ ID NO: 2.

In some embodiments, the ketoreductase can be present in the form of whole cells, including whole cells transformed with polynucleotide constructs expressing wild type or engineered ketoreductases. In some embodiments, the ketoreductase can present as cell extracts and/or lysates thereof, and may be employed in a variety of different forms, including solid (e.g., lyophilized, spray-dried, and the like) or semisolid (e.g., a crude paste). In some embodiments of the process, the ketoreductase is isolated, and can be in substantially purified form.

In the cofactor regenerating process carried out by the ketoreductase, an alcohol is used as the substrate reductant for the generation of reduced cofactor NADH or NADPH. As noted above, while primary alcohols substrates recognized by the ketoreductase, such as ethanol, can be used, preferable are secondary alcohols, particularly lower secondary alcohols. Suitable secondary alcohols include lower secondary alkanols and aryl-alkyl carbinols. Examples of lower secondary alcohols include isopropanol, 2-butanol, 3-methyl-2-butanol, 2-pentanol, 3-pentanol, 3,3-dimethyl-2-butanol, and the like. Suitable aryl-alkyl carbinols include unsubstituted and substituted 1-arylethanols. In some embodiments, the secondary alcohol is isopropanol.

The alcohol, particularly a secondary alcohol (e.g., isopropanol), can be present at about 1% to 60% v/v, about 1% to 50% v/v, about 1% to 40% v/v, about 1% to 30% v/v, about 1% to 20% v/v, or about 1% to 10% v/v of the reaction medium. In some embodiments, the alcohol can be present at about 10% to 60% v/v, about 10% to 50% v/v, about 10% to 40% v/v, about 10% to 30% v/v, or about 10% to 20% v/v of the reaction medium. In some embodiments, the alcohol can be present at about 20% to 60% v/v, about 20% to 50% v/v, about 20% to 40% v/v, or about 20% to 30% v/v of the reaction medium. The amount of alcohol useful in the process can be determined based on the activities of the amino acid dehydrogenase and the ketoreductase in the presence of a defined amount of alcohol.

In some embodiments of the process, the product formed from the ketoreductase can be removed from the reaction medium to improve conversion of the alcohol to the corresponding carbonyl product, and thereby pushing the equilibrium of the process to the reduction of NAD+ or NADP+ to NADH or NADPH. For instance, where the carbonyl product is volatile, the product can be removed by sparging the reaction medium with an non-reactive gas or by lowering the vapor pressure of the reaction medium and removing the volatile carbonyl product. In some embodiments of the process, the alcohol substrate for the ketoreductase is a lower secondary alcohol, and the corresponding lower alkyl ketone formed from the lower secondary alcohol is removed from the reaction medium. In some embodiments, where the alcohol is isopropanol, the product acetone can be removed by sparging the reaction medium with a non-reactive gas, such as nitrogen, or by applying a vacuum to the reaction medium and removing the acetone by condensation.

Where appropriate for use in the processes, the amino acid dehydrogenases and ketoreductase enzymes present in cells, such as engineered enzymes expressed in host cells, can be recovered from the cells and or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as $E.$ $coli$, are commercially available under the trade name Cel-Lytic B™ from Sigma-Aldrich of St. Louis Mo. The cell extracts or cell lysates may be partially purified by precipitation (ammonium sulfate, polyethyleneimine, heat treatment or the like, followed by a desalting procedure prior to lyophilization (e.g., ultrafiltration, dialysis, and the like). Any of the cell preparations may be stabilized by crosslinking using known crosslinking agents, such as, for example, glutaraldehyde or immobilization to a solid phase (e.g., Eupergit C, and the like).

The reactions described herein are generally carried out in a solvent. Suitable solvents include water, organic solvents (e.g., ethyl acetate, butyl acetate, 1-octanol, heptane, octane, methyl t-butyl ether (MTBE), toluene, and the like), and ionic liquids (e.g., 1-ethyl 4-methylimidazolium tetrafluoroborate, 1-butyl-3-methylimidazolium tetrafluoroborate, 1-butyl-3-methylimidazolium hexafluorophosphate, and the like). In some embodiments, aqueous solvents, including water and aqueous co-solvent systems, can be used.

Exemplary aqueous co-solvent systems have water and one or more organic solvent. In general, an organic solvent component of an aqueous co-solvent system is selected such that it does not significantly inactivate the enzymes (i.e., amino acid dehydrogenase and ketoreductase). Appropriate co-solvent systems can be readily identified by measuring the enzymatic activity of the specified enzyme with a defined substrate of interest in the candidate solvent system, utilizing an enzyme activity assay, such as those described herein.

The organic solvent component of an aqueous co-solvent system may be miscible with the aqueous component, providing a single liquid phase, or may be partly miscible or immiscible with the aqueous component, providing two liquid phases. Generally, when an aqueous co-solvent system is employed, it is selected to be biphasic, with water dispersed in an organic solvent, or vice-versa. Generally, when an aqueous co-solvent system is utilized, it is desirable to select an organic solvent that can be readily separated from the aqueous phase. In general, the ratio of water to organic solvent in the co-solvent system is typically in the range of from about 90:10 to about 10:90 (v/v) organic solvent to water, and between 80:20 and 20:80 (v/v) organic solvent to water. The co-solvent system may be pre-formed prior to addition to the reaction mixture, or it may be formed in situ in the reaction vessel.

During the course of the amino acid dehydrogenase and ketoreductase mediated process, the pH of the reaction medium may change. The pH of the reaction medium may be maintained at a desired pH or within a desired pH range by the addition of an acid or a base during the course of the reaction. Alternatively, the pH may be controlled by using an aqueous solvent that comprises a buffer. Suitable buffers to maintain desired pH ranges are known in the art and include, for example, phosphate buffer, triethanolamine buffer, and the like. Combinations of buffering and acid or base addition may also be used. Typically, bases added to unbuffered or partially buffered reaction mixtures over the course of the reduction are added in aqueous solutions.

In carrying out embodiments of the process described herein, either the oxidized or reduced form of the cofactor may be provided initially. As described above, the cofactor regenerating system converts oxidized cofactor to its reduced form (or vice-versa), which is then utilized in the reduction (or oxidation) of the substrate.

The solid reactants (e.g., enzyme, salts, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a pre-chilled lyophilization chamber, followed by the application of a vacuum. After the removal of water from the samples, the temperature is typically raised to about 4° C. before release of the vacuum and retrieval of the lyophilized samples.

The quantities of reactants used in the reduction reaction will generally vary depending on the quantities of product desired, and concomitantly, the amount of substrate employed. The following guidelines can be used to determine the amounts of amino acid dehydrogenase, ketoreductase, and cofactor. Those having ordinary skill in the art will readily understand how to vary these quantities to tailor them to the desired level of productivity and scale of production. Appropriate quantities of cofactor regenerating system may be readily determined by routine experimentation based on the amount of amino acid dehydrogenase and ketoreductase utilized.

The order of addition of reactants is not critical. The reactants may be added together at the same time to a solvent (e.g., monophasic solvent, biphasic aqueous co-solvent system, and the like), or alternatively, some of the reactants may be added separately, and some together at different time points.

For improved mixing efficiency when an aqueous co-solvent system is used, the amino acid dehydrogenase and the ketoreductase may be added and mixed into the aqueous phase first. The organic phase may then be added and mixed in, followed by addition of the enzyme substrates. Alternatively, the enzymes may be premixed in the organic phase, prior to addition to the aqueous phase.

Suitable conditions for carrying out the amino acid dehydrogenase/ketoreductase mediated process described herein include a wide variety of conditions which can be optimized by routine experimentation that includes, but is not limited to, contacting the enzymes and substrates at an experimental pH and temperature and detecting product, for example, using the methods described in the Examples provided herein.

Generally, the process can be carried out at a pH of about 11 or below, usually in the range of from about 8.0 to about 11. In some embodiments, the process may be carried out a neutral pH, i.e., about 7.0. The optimal pH of the reaction medium can be determined based on the pH sensitivities of the amino acid dehydrogenase and ketoreductase enzymes. In some embodiments, the process is carried out at a pH of about 9.5 or below, usually in the range of from about 8.5 to about 9.5, and in some embodiments at a pH of about 8.75 to about 9.25, and in some embodiments the process is carried out at about pH 9. In some embodiments, the process may can be carried out at a pH of about 9 to about 11, particularly at about pH 10 to about 11.

In some embodiments, the process described herein can be carried out at a temperature in the range of from about 15° C. to about 75° C. In some embodiments, the reaction is carried out at a temperature in the range of from about 20° C. to about 55° C. In some embodiments, it is carried out at a temperature in the range of from about 20° C. to about 45° C. In some embodiments, the process is carried out at a temperature of about 35° C. to about 40° C. The reaction may also be carried out under ambient conditions.

The process is generally allowed to proceed until there is no further conversion or substantial conversion of substrate (e.g., oxo acid) to the product (e.g., amino acid) or until there is essentially complete, or nearly complete, conversion of substrate to product. Conversion of substrate to product can be monitored using known methods by detecting substrate and/or product. Suitable methods include gas chromatography, HPLC, and the like. Conversion yields of the product amino acid generated in the reaction mixture can be greater than about 50%, greater than about 60%, greater than about 70%, greater than about 80%, greater than 90%, and are often greater than about 97%.

In some embodiments, the process described herein can be used in the conversion of a compound of formula I which is 3,3-dimethyl-2-oxobutanoic acid (also referred to herein as "trimethylpyruvic acid" or "TMP") to the chiral amino acid (S)-2-amino-3,3-dimethylbutanoic acid (also referred to herein as "L-tert-leucine"), where the amino acid dehydrogenase comprises a L-leucine dehydrogenase ("LeuDH"), as illustrated by Scheme 2.

Scheme 2

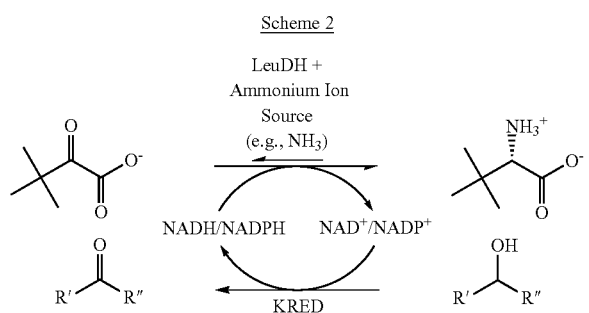

The chiral amino acid L-tert-leucine is useful in the synthesis of intermediates, particularly advanced pharmaceutical intermediate used in the preparation of drug compounds, e.g., atazanavir, boceprevir, and telaprevir.

In some embodiments, the process for producing L-tert-leucine can comprise contacting the substrate 3,3-dimethyl-2-oxobutanoic acid with a reaction medium comprising a L-leucine dehydrogenase, an ammonium ion donor, NAD$^+$/NADH or NADP$^+$/NADPH, and a cofactor regenerating system comprising a ketoreductase and an alcohol, under suitable reaction conditions to convert the 3,3-dimethyl-2-oxobutanoic acid to product (S)-2-amino-3,3-dimethylbutanoic acid, and the alcohol to the corresponding carbonyl compound. In particular, the alcohol is a secondary alcohol, as described herein.

In some embodiments, the L-leucine dehydrogenase used in the process can be a wild type leucine dehydrogenase or an engineered leucine dehydrogenase. L-leucine dehydrogenases can be from genus *Bacillus, Clostridium, Corynebacterium, Geobacillus, Natronobacterium, Thermoactinomyces, Thermos, Thermomicrobium*, or *Carderia*.

In some embodiments, the leucine dehydrogenase is from *Bacillus acidokaludarius, Bacillus brevis, Bacillus caldolyticus, Bacillus cereus, Bacillus megaterium, Bacillus mesentericus, Bacillus mycoides, Bacillus natto, Bacillus pumilus, Bacillus sphaericus, Bacillus stearothermophilus, Bacillus subtilis, Clostridium thermoaceticum, Corynebacterium pseudodiphtheriticum, Geobacillus stearothermophilus, Natronobacterium magadii*, or *Thermoactinomyces intermedius*.

The process disclosed herein could be used with any wild-type L-leucine dehydrogenase. Sequences of such wild-type enzymes are publicly available, for example from the GenBank database available at the NCBI web-site.

A few exemplary wild-type leucine dehydrogenase enzyme sequences listed by GenBank accession include: leucine dehydrogenase [*Geobacillus stearothermophilus*] gi|34014423|dbj|BAC81829.1|; leucine dehydrogenase [*Geobacillus stearothermophilus*] gi|143145|gb|M22977.1|; leucine dehydrogenase [*Geobacillus stearothermophilus*] gi|3401442|dbj|AB103384.1|; leucine dehydrogenase [*Bacillus licheniformis*] gi|1477946|gb|AAB36205.1||bbm|385403|bbs|177171 [1477946]; LEUCINE-DEHYDROGENASE [*Bacillus cereus*] gi|6741939|emb|CAB69610.1|[6741939]; leucine dehydrogenase [*Streptosporangium roseum* DSM 43021] gi|271970173|gnl|REF_jgi|Sros_8995|ref|YP_003344369.1|[271970173]; leucine dehydrogenase [*Streptosporangium roseum* DSM 43021] gi|270513348|gnl|jgi|Sros_8995|gb|ACZ91626.1| [270513348]; leucine dehydrogenase [*Natranaerobius thermophilus* JW/NM-WN-LF] gi|179351985|gnl|jgi|Nther_2701|gb|ACB86255.1| [179351985]; leucine dehydrogenase [*Natranaerobius thermophilus* JW/NM-WN-LF] gi|1179351644|gnl|jgi|Nther_2349|gb|ACB85914.1| [179351644]; leucine dehydrogenase [*Natranaerobius thermophilus* JW/NM-WN-LF] gi|179350985|gnl|jgi|Nther_1681|gb|ACB85255.1| [179350985]; leucine dehydrogenase [*Shewanella amazonensis* SB2B] gi|19767702|gnl|jgi|Sama_2067|gb|ABM00273.1| [119767702]; leucine dehydrogenase [*Shewanella* sp. ANA-3] gi|l 1761252||gnl|gi|Shewana3_1742|gb|ABK47975.1| [117612521]; leucine dehydrogenase [*Shewanella frigidimarina* NCIMB 400] gi|114334729|gnl|gi|Sfri_2265|gb|ABI72111.1| [114334729]; leucine dehydrogenase [*Shewanella* sp. MR-7] gi|13888616|gnl|jgi|Shewmr7_1673|gb|ABI42667.1 [|113888616]; leucine dehydrogenase [*Shewanella* sp. MR-4] gi|l 13884623|gnl|jgi|Shewmr4_1598|gb|ABI38675.1| [113884623]; leucine dehydrogenase [*Chelativorans* sp.

BNC1] gi|110286554|gnl|jgi|Meso_3241|gb|ABG64613.1| [110286554]; leucine dehydrogenase [*Pseudoalteromonas atlantica* T6c] gi|109701583|gnl|jgi|Pat|_2995|gb|ABG41503.1| [109701583]; leucine dehydrogenase [*Rubrobacter xylanophilus* DSM 9941] gi|1108766512|gnl|jgi|Rxyl_2467|gb|ABG05394.1| [108766512]; leucine dehydrogenase [*Chlamydophila pneumoniae* TW-183] gi|33236793|gb|AAP98880.1|||gnl|byk|CpB0951 [33236793]; Leucine dehydrogenase [*Bacillus cereus* m1293] gi|229198293|ref|ZP_04325000.1|gnl|WGS: NZ_ACLS01|bcere0001_38230[229198293]; Leucine dehydrogenase [*Bacillus cereus* ATCC 10876] gi|229192377|ref|ZP_04319341.1|||gnl|WGS: NZ_ACLT01|bcere0002_40300[229192377]; Leucine dehydrogenase [*Bacillus cereus* BGSC 6E1] gi|229186408|ref|ZP_04313572.1|||gnl|WGS: NZ_ACLU01|bcere0004_39530[229186408]; Leucine dehydrogenase [*Bacillus cereus* 172560W] gi|229180445|ref|ZP_04307788.1|||gnl|WGS: NZ_ACLV01|bcere0005_37900[229180445]; Leucine dehydrogenase [*Bacillus cereus* MM3] gi|229174841|ref|ZP_04302361.1|||gnl|WGS: NZ_ACLW01|bcere0006_39250[229174841]; Leucine dehydrogenase [*Bacillus cereus* AH621] gi|229168909|ref|ZP_04296626.1|gnl|WGS: NZ_ACLX01|bcere0007_38620[229168909]; Leucine dehydrogenase [*Bacillus cereus* R309803] gi|229163100|ref|ZP_04291056.1|||gnl|WGS: NZ_ACLY01|bcere0009_38690[229163100]; Leucine dehydrogenase [*Bacillus cereus* ATCC 4342] gi|229157746|ref|ZP_04285821.11|gnl|WGS:NZ_ACLZ01 bcere0010_39270[229157746]; Leucine dehydrogenase [*Bacillus cereus* m1550] gi|229152367|ref|ZP_04280559.1|gnl|WGS:NZ_ACMA01 bcere0011_39050[229152367]; Leucine dehydrogenase [*Bacillus cereus* BDRD-ST24] gi|229146739|ref|ZP_04275105.1|||gnl|WGS:NZ_ACMB01 bcere0012_38800[229146739]; Leucine dehydrogenase [*Bacillus cereus* BDRD-ST26] gi|229140899|ref|ZP_04269444.1|||gnl|WGS:NZ_ACMC01 bcere0013_39930[229140899]; Leucine dehydrogenase [*Bacillus cereus* BDRD-ST196] gi|229134979|ref|ZP_04263785.1|||gnl|WGS:NZ_ACMD01 bcere0014_38860[229134979]; and Leucine dehydrogenase [*Bacillus cereus* BDRD-Cer4] gi|229129445|ref|ZP_04258416.1|||gnl|WGS: NZ_ACME01|bcere0015_38880[229129445].

Leucine dehydrogenases useful with the process of the present disclosure include an L-leucine dehydrogenase from *Bacillus cereus* such as the enzyme disclosed in e.g., U.S. Pat. No. 5,854,035, which is hereby incorporated by reference herein.

Exemplary leucine dehydrogenases useful with process of the disclosure can also be obtained from *Geobacillus stearothermophilus* (e.g., gi|34014423|dbj|BAC81829.1|; gi|143145|gb|M22977.1|; gi|34014421|dbj|AB103384.1|). In one embodiment, an L-leucine dehydrogenase from *G. stearothermophilus* useful with the present process comprises an amino acid sequence of SEQ ID NO: 26. Further suitable LeuDH enzymes useful with the present process can be engineered by site-directed mutagenesis and/or directed evolution methods using the polynucleotide of SEQ ID NO: 25, which encodes the wild-type LeuDH of SEQ ID NO: 26.

As noted above, the ammonium ion donor in the process mediated by the leucine dehydrogenase can be any suitable ammonium ion donor, which provides the $NH_3$ for formation of the amino acid. Exemplary ammonium source includes, among others, various ammonium salts, such as ammonium halide (e.g., ammonium chloride), ammonium formate, ammonium sulfate, ammonium phosphate, ammonium nitrate, ammonium tartrate, and ammonium acetate. In particular, the process for forming L-tert-leucine with leucine dehydrogenase can use ammonium chloride as the ammonium donor.

In the process for formation of L-tert-leucine, the ketoreductase of the cofactor regenerating system can be any suitable ketoreductase capable of forming reduced cofactor NADH and/or NADPH utilizing the oxidization of the alcohol to the corresponding carbonyl compound to drive the reaction towards reduced cofactor formation. As described herein, the ketoreductase can be a wild type ketoreductase, or an engineered ketoreductase. The engineered ketoreductase can have an improved enzyme property, such as improvements in enzymatic activity, thermostability, solvent stability, pH stability, inhibitor resistance, or cofactor preference. Ketoreductases found in or derived from any number of organisms, as discussed above, can be used in conjunction with the leucine dehydrogenase.

In some embodiments, the ketoreductase is an engineered enzyme derived from *Candida magnoliae*, *Lactobacillus kefir*, *Lactobacillus brevis*, *Lactobacillus minor*, *Saccharomyces cerevisiae* or *Novosphingobium aromaticivorans*, as discussed above. Exemplary engineered ketoreductases useful with the leucine dehydrogenase in forming L-tert-leucine can comprise an amino acid sequence selected from the group consisting of SEQ ID NO: 4, 6, 8, 10, 12, 14, 16, 18, 20, 22, and 24.

In the leucine dehydrogenase mediated process, the substrate alcohol for the ketoreductase can comprise any alcohol that is recognized and converted by the ketoreductase to the corresponding carbonyl compound. The alcohol can be a primary alcohol or a secondary alcohol. An exemplary primary alcohol recognized by ketoreductases is ethanol. In some embodiments, the alcohol is a suitable secondary alcohol, including lower secondary alkanols and aryl-alkyl carbinols, as noted above. Exemplary secondary alcohol for use in the cofactor regenerating system with the leucine dehydrogenase includes, by way of example and not limitation, include isopropanol, 2-butanol, 3-methyl-2-butanol, 2-pentanol, 3-pentanol, 3,3-dimethyl-2-butanol, and the like, particularly isopropanol.

The alcohol, particularly a secondary alcohol, such as isopropanol, can be present at about 1% to 60% v/v, about 1% to 50% v/v, about 1% to 40% v/v, about 1% to 30% v/v, about 1% to 20% v/v, or about 1% to 10% v/v of the reaction medium. In some embodiments, the alcohol can be present at about 10% to 60% v/v, about 10% to 50% v/v, about 10% to 40% v/v, about 10% to 30% v/v, or about 10% to 20% v/v of the reaction medium. In some embodiments, the alcohol can be present at about 20% to 60% v/v, about 20% to 50% v/v, about 20% to 40% v/v, or about 20% to 30% v/v of the reaction medium. In some embodiments, the process with the leucine dehydrogenase has about 5% to 20% isopropanol, particularly 5% to 15% isopropanol. An exemplary amount of isopropanol is about 8% to 12% of the reaction medium v/v. In some embodiments, the secondary alcohol is present in at least 1.5 fold stoichiometric excess of substrate.

Generally, the process with the leucine dehydrogenase can be carried out at a pH of about 11 or below, usually in the range of from about 8.0 to about 11. In some embodiments, the process is carried out at a pH of about 9.0 or below, usually in the range of from about 8.5 to about 9.0.

In some embodiments, the process for forming L-tert-leucine with leucine dehydrogenase, can be carried out at a pH of about 9 to about 11, particularly at about pH 9 to 10, more particularly at about pH 9.5. In some embodiments, the process may be carried out a neutral pH, i.e., about 7.0. It is to be understood that the pH of the reaction medium for the formation of L-tert-leucine can be determined based on the activities of the leucine dehydrogenase and ketoreductase at different pHs.

In some embodiments, the process described herein can be carried out at a temperature in the range of from about 15° C. to about 75° C. In some embodiments, the reaction is carried out at a temperature in the range of from about 20° C. to about 55° C. In some embodiments, it is carried out at a temperature in the range of from about 20° C. to about 45° C. In some embodiments, the process is carried out at a temperature of about 35° C. to about 45° C. The reaction may also be carried out under ambient conditions.

In view of the foregoing, a process for producing (S)-2-amino-3,3-dimethylbutanoic acid (also referred to herein as "L-tert-leucine"), can comprise: contacting 3,3-dimethyl-2-oxobutanoic acid (also referred to herein as "trimethyl pyruvic acid", "TMP", or "trimethyl pyruvate") with a reaction medium comprising a leucine dehydrogenase, an ammonium ion donor, $NAD^+$/NADH or $NADP^+$/NADPH, and a cofactor recycling system comprising a ketoreductase and a lower secondary alcohol, under conditions where the 3,3-dimethyl-2-oxobutanoic acid is converted to (S)-2-amino-3,3-dimethylbutanoic acid, wherein the 3,3-dimethyl-2-oxobutanoic acid is at about 75 g/L to 125 g/L, the cofactor is at about 0.30 g/L to 0.70 g/L, and the leucine dehydrogenase and ketoreductase are each independently at about 0.5 to about 1.0 g/L.

The process for forming L-tert-leucine with a leucine dehydrogenase can be carried out with whole cells or in a cell free system. In some embodiments, the leucine dehydrogenase can be present in whole cells while the ketoreductase is present in a cell free system. Conversely, in some embodiments, the leucine dehydrogenase can be present in cell free system while the ketoreductase is present in whole cells. In some embodiments, the whole process is carried out in a cell free system, where the leucine dehydrogenase and the ketoreductase is present a crude extract or in isolated form. In some embodiments, the leucine dehydrogenase and ketoreductase is provided in substantially purified form.

In some embodiments, the process for forming L-tert-leucine of the present disclosure can be carried out wherein the leucine dehydrogenase polypeptide and/or the ketoreductase polypeptide is immobilized on a surface, for example wherein the enzyme is linked to the surface of a solid-phase particle (e.g., beads) or resin that is present in the solution or otherwise is contacted by the solution (e.g., a flow-through system in a column). Methods for linking (covalently or non-covalently) enzymes to solid-phase supports or particles (e.g., porous or non-porous beads, resins, or solid supports) such that they retain activity for use in industrial bioreactors are known in the art (see e.g., Hermanson, G. T., *Bioconjugate Techniques*, Second Edition, Academic Press; (2008), and "Bioconjugation Protocols: Strategies and Methods," in *Methods in Molecular Biology*, C. M. Niemeyer ed., Humana Press (2004); Mateo et al., "Epoxy sepabeads: a novel epoxy support for stabilization of industrial enzymes via very intense multipoint covalent attachment," Biotechnol Prog. 18(3):629-34 (2002); the disclosures of which are incorporated herein by reference). Useful solid supports can be in the form of beads, spheres, particles, granules, a gel, a membrane or a surface, can be porous or non-porous, can have swelling or non-swelling characteristics, can be composed of organic polymers, such as polystyrene, polyethylene, polypropylene, polyfluoroethylene, polyethyleneoxy, and polyacrylamide, as well as co-polymers and grafts thereof, or can be composed of inorganic solids, such as glass, silica, controlled pore glass (CPG), reverse phase silica or metal, such as gold or platinum. A variety of useful solid supports for the immobilization of enzymes are commercially available (e.g., SEPABEADS resins; available from Sigma-Aldrich, USA).

In some embodiments of the process using immobilized enzymes, the immobilized LeuDH and KRED polypeptides can be on different particles, which can be mixed in the reaction chamber, or in some embodiments, both enzymes can be immobilized on the same particles. In some embodiments, the methods using immobilized polypeptides can be carried out wherein the method further comprises a step of isolating or separating the immobilized enzymes from the reaction solution containing the product so that the enzymes can be recycled. In continuous flow-through embodiments, the particles comprising the immobilized LeuDH and/or KRED are maintained in a reaction chamber or column and the reacting solution flows through at a rate (and under suitable conditions) to allow for complete conversion of the substrate the reaction solution to product whereupon it exits the reaction chamber or column.

As noted above, to facilitate the reaction toward formation of product, the process of can further comprise removing from the reaction medium the carbonyl product formed from the alcohol used as the substrate to the ketoreductase. In the exemplary embodiments using isopropanol as the alcohol, the corresponding product acetone can be removed by sparging the reaction medium with an inert gas, such as nitrogen gas, or by lowering the pressure of the reaction medium and trapping the volatile acetone in a condenser.

As will be apparent to the skilled artisan, the process for forming L-tert-leucine can be varied with respect to amounts of L-leucine dehydrogenase, 3,3-dimethyl-2-oxobutanoic acid, cofactor, ketoreductase, and alcohol for the efficient conversion of the substrate to the product (S)-2-amino-3,3-dimethylbutanoic acid. In some embodiments, at a substrate loading of at about 75 g/L to 125 g/L, the process is capable of converting at least 80%, at least 85%, at least 90%, at least 91%, at least 92%, at least 93%, at least 94%, at least 95%, at least 96%, at least 97%, at least 98%, at least 99% or about 100% of the substrate to the corresponding product.

In some embodiments, the present disclosure provides a process for preparing an N-protected chiral amino acid compound, where the process comprises: (i) a biocatalytic step for converting a compound of formula I to a chiral amino acid compound of formula IIa; and (ii) a chemical step where the amino acid compound of formula IIa is converted to an N-protected chiral amino acid compound.

The present disclosure contemplates that the biocatalytic step for converting a compound of formula I to a chiral amino acid compound of formula IIa may be carried out using any of the processes disclosed herein wherein the biocatalytic step comprises contacting a compound of formula I with a reaction medium comprising an amino acid dehydrogenase, an ammonium ion donor, $NAD^+$/NADH or $NADP^+$/NADPH, and a cofactor regenerating system comprising a ketoreductase and a lower secondary alcohol under suitable conditions where the compound of formula I is converted to the chiral amino acid compound of formula IIa and the lower secondary alcohol is converted to a ketone.

The present disclosure contemplates that the chemical step where the amino acid compound of formula IIa is converted to an N-protected chiral amino acid compound is carried out by contacting the amino acid compound of formula IIa (produced in the biocatalytic step) with a N-protecting group reagent under conditions where the N-protecting group reacts with the amine group nitrogen of the compound of formula IIa.

Examples of such N-protecting groups useful in the processes of the disclosure include the formyl group, the trityl group, the methoxytrityl group, the tosyl group, the phthalimido group, the acetyl group, the trichloroacetyl group, the chloroacetyl, bromoacetyl, and iodoacetyl groups, benzyloxycarbonyl (Cbz), methoxycarbonyl (MOC), 9-fluorenylmethoxycarbonyl (FMOC), 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), trihaloacetyl, benzyl, benzoyl, and nitrophenylacetyl and the like. Further examples of protecting groups useful with the embodiments of the present disclosure can be found in P. G. M. Wuts and T. W. Greene, "Greene's Protective Groups in Organic Synthesis—Fourth Edition," John Wiley and Sons, New York, N.Y., 2007, Chapter 7 ("Greene").

In one embodiment, the compound of formula I is trimethylpyruvic acid (TMP) and the chiral amino acid compound of formula IIa is L-tert-leucine. According to the process of the present disclosure an N-protected L-tert-leucine (e.g., an L-tert-leucine with its amine group nitrogen protected) can be prepared with e.g., a t-butoxycarbonyl (BOC), benzyloxycarbonyl (Cbz), 9-fluorenylmethoxycarbonyl (FMOC), or methoxycarbonyl (MOC) protecting group. Processes for preparing the BOC and MOC protected L-tert-Leucine are described in Examples 1-4.

Various features and embodiments of the disclosure are illustrated in the following representative examples, which are intended to be illustrative, and not limiting.

EXAMPLES

Example 1: Biocatalytic Process for Preparation of Enantiomerically Pure L-Tert-Leucine from Trimethylpyruvic Acid (TMP)

This Example illustrates a biocatalytic process for production of enantiomerically pure L-tert-leucine from trimethylpyruvic acid at a 20 g scale using leucine dehydrogenase (LeuDH) in the presence of a ketoreductase (KRED) recycling system.

Materials

The materials used and their sources are provided in Table 5. Specific vendors and grades are given for commercially available inputs, although it is expected that the source of such reagents would not have an impact upon the reaction.

TABLE 5

Materials List

| Material | Amount |
| --- | --- |
| Trimethylpyruvic acid (60% aqueous solution) | 20 g (33.4 mL) |
| Water | 118.6 mL |
| Ammonium hydroxide (28-30% aqueous solution) | 19 mL |
| Ammonium chloride | 9.0 g |
| Isopropanol (min 99.7%) | 20 mL |
| β - NAD$^+$ | 100 mg |

TABLE 5-continued

Materials List

| Material | Amount |
| --- | --- |
| Leucine dehydrogenase (LeuDH) of SEQ ID NO: 26 | 150 mg |
| Ketoreductase (KRED) of SEQ ID NO: 18 | 150 mg |

Summary of Reaction Conditions

A summary of the reaction conditions used in the biocatalytic process are shown below in Table 6.

TABLE 6

Reactant parameters and conditions for biocatalytic process

| Trimethylpyruvic acid (TMP) | 100 g/L |
| --- | --- |
| Ammonium chloride | 1.1 equiv |
| pH | 9.0 |
| IPA | 10% |
| β - NAD$^+$ | 0.50 g/L |
| LeuDH of SEQ ID NO: 26 | 0.75 g/L |
| KRED of SEQ ID NO: 18 | 0.75 g/L |
| Temperature | 40° C. |

Reaction Protocol

A 250 mL 2-neck round bottom flask was equipped with pH probe and a magnetic stirrer. The pH probe also served as an internal thermometer. The flask was charged sequentially with 100 mL water and 20.0 g (33.4 mL) of trimethylpyruvic acid. The resulting aqueous solution was ~pH 1.1 (measured at 23° C.) and was stirred for 10 minutes at 400 rpm at room temperature to obtain homogeneity. The solution was cooled to 15° C. using ice water bath. Ammonium hydroxide was added in portions to neutralize the acid and attain a pH between 7 and 7.5, maintaining the temperature below 20° C. during addition. Approximately 13 mL of ammonium hydroxide (28-30% aqueous solution) adjusted the pH to 7.34 at 21° C. Ammonium chloride (1.1 equiv, 9.0 g) was added and stirred until a clear solution was obtained. After addition of ammonium chloride, reaction mixture was allowed to reach room temperature and the pH at room temperature approximately 7.0. The reaction mixture was readjusted to pH 9.0 by adding ammonium hydroxide in portions, maintaining the temperature below 25° C. during addition. Approximately 6 mL of ammonium hydroxide (28-30% aqueous solution) adjusted the pH to 9.03 at 22° C. The pH was found to have a significant impact on the rate of reaction Reactions did not proceed to complete conversion in 24 h when NaOH was used to adjust pH to pH 9.5 or above. 20 mL isopropanol (IPA) was added to the reaction mixture. The pH dropped to 8.95 upon addition of IPA, but no further re-adjustment to pH 9.0 was carried out. NAD (100 mg) was charged to the stirred mixture as a powder and 18.6 mL of water as added to the reaction mixture to adjust the final volume to 200 mL. The leucine dehydrogenase (LeuDH) of SEQ ID NO: 26 (150 mg) and the engineered ketoreductase (KRED) of SEQ ID NO: 18 (150 mg) biocatalysts were charged to the stirred mixture as powders. The reaction mixture was heated to 40° C. (internal temperature) stirring at 600 rpm. The final temperature was reached within 30 min. The reaction course was followed by taking samples periodically out of the reaction mixture and analyzing as described below. For the purpose of monitoring the reaction, t=0 was the time at which the KRED was added into the reaction mixture. After in-process analyses indicated maximum conversion, the reaction was cooled to room temperature (in this Example, the reaction was stirred for a total time of 24 h). As shown by the reaction profile based on the in-process analyses (described further below) provided in Table 7 below, the biocatalytic reaction achieved nearly 88% conversion of TMP substrate to L-tert-leucine product in only 7.5 hours, and complete (i.e., 99.9%) conversion of substrate to L-tert-leucine product in 24 hours.

TABLE 7

Reaction profile

| Time (h) | % Conversion |
|---|---|
| 0 | 0 |
| 1.5 | 53.7 |
| 3 | 64.0 |
| 4.5 | 75.6 |
| 6 | 83.7 |
| 7.5 | 87.9 |
| 22 | 99.5 |
| 24 | 99.9 |

White turbidity was observed as reaction progressed and the pH of the reaction mixture after complete conversion was 8.83 at room temperature. A sample (10 mL) of the reaction mixture was taken and heated at 40° C. for an additional 24 h. No increase in impurities was observed by GC analysis.

L-Tert Leucine Product Isolation and Work-Up

The reaction mixture was adjusted to pH 4.5 using 6.0 M HCl solution under controlled exothermic conditions. Celite (3.0 g) was added at room temperature and stirred to obtain homogeneity. The mixture was filtered through a sintered glass funnel and the filter cake washed with 10 mL of water. The combined aqueous solution was concentrated to about one-third the original volume. Precipitation of a white solid was observed during concentration. The suspension was cooled in an ice bath for a few hours and the solid was filtered, washed with 20 mL of a 1:1 mixture of isopropanol:water followed by 20 mL of acetonitrile. A repeat washing with 1:1 isopropanol:water (50 mL) and acetonitrile (50 mL) afforded 3.0 g (approx. yield=50%) of white solid. The solid was identified as the desired product, L-tert-leucine, with about 90% purity when compared with a standard sample of L-tert-leucine (peak area by HPLC-ELSD).

Analytical Methods

Analytical methods used in the biocatalytic process and described below include: Method 1, a GC analysis method used to monitor % conversion of trimethylpyruvic acid substrate to L-tert-leucine product; Method 2, an HPLC-UV-ELSD method to monitor trimethylpyruvic acid substrate to and L-tert-leucine product in the reaction; and Method 3, an HPLC method to determine the enantiomeric excess of L-tert-leucine formed during the course of the reaction. Results obtained by the Method 1 were verified using Method 2.

Method 1: GC Analysis Method for Monitoring % Conversion

Sample Preparation:

In a 1.5 mL glass vial, samples from the reaction mixture (5 µL) were diluted in 1.0 mL of acetonitrile containing 10 µL of pyridine. Methyl chloroformate (10 µL) was added and the mixture was agitated for a few seconds. The exothermic reaction accompanied by release of $CO_2$ was left standing until the precipitate settled. A sample (300 µL) from the supernatant of the derivatized reaction sample was taken and analyzed by gas chromatography (GC). A summary of the analytical parameters and conditions are provided in Table 8 below.

TABLE 8

| Instrument | Agilent 6890N series |
|---|---|
| Column: | HP-5 (30.0 µm × 320 µm × 0.25 µm nominal) |
| Temperature profile: | 90° C. (hold for 2.8 min) then ramp to 210° C. @ 20° C./min |
| Pressure: | 12 psi (constant) |
| Inlet: | 250° C. |
| Split ratio | 20:1 |
| Detector | FID, 250° C. |
| Run time | 8.8 min |
| Retention times | Trimethylpyruvic acid methyl ester (Peak 1): 2.50 min Derivatized L-tert-leucine (Peak 2): 6.6 min |

The % conversion based on consumption of trimethylpyruvic acid was calculated as follows:

$$\% \text{ Conversion} = \frac{(\text{Area of Peak 1})_{t=0} - (\text{Area of Peak 1})_{t=x}}{(\text{Area of Peak 1})_{t=0}} \times 100$$

Method 2: HPLC-UV-ELSD Analysis Method for Monitoring % Conversion

HPLC Sample Preparation:

20 µL of the reaction mixture was taken and added to 980 µL of mobile phase A. Injection is neat into the HPLC equilibrated and set up according to the analytical parameters and conditions are provided in Table 9 below.

TABLE 9

| Instrument | Agilent HPLC 1200 series |
|---|---|
| Column | Mightysil RP18 GP, 250 × 4.6 mm, 5 µm (1 × Aqua R18 guard column before & after analytical column). |
| Mobile Phase | A: 76% 20 mM $NH_4OAc$, pH 4.87 + 0.3 mM dodecyltriethylammonium phosphate [Regis Cat No: 404021] B: 24% MeCN |
| Flow rate | 1.0 mL/min |
| Run Time | 15 min |
| ELSD detector temperature | 35° C. |
| Column temperature | 29° C. |
| Injection volume | 10 µL |
| Gain | 3 |
| UV Wavelength | 230 nm |
| Retention Times | Peak 1 (L-tert-leucine): 2.725 min Peak 2 (TMP): 13.587 min |

The % conversion is calculated as follows:

$$\% \text{ Conversion} = \frac{(\text{Area of Peak 1})}{[(\text{Area of Peak 1}) + (\text{Area of Peak 2} \times \text{Response factor})]} \times 100$$

where the Response Factor is calculated as follows:

$$\text{Response Factor} = \frac{(\text{Area of Peak 1 at time} = x)}{[(\text{Area of Peak 2 at time} = 0) - (\text{Area of Peak 2 at time} = x)]}$$

Method 3: HPLC Analysis of Enantiomeric Purity

HPLC Sample Preparation:

10 µL from the reaction mixture was taken and added 990 µL of mobile phase in a 2 mL HPLC glass vial. Injection is neat into the HPLC equilibrated and set up according to the analytical parameters and conditions are provided in Table 10 below.

TABLE 10

| | |
|---|---|
| Instrument | Agilent HPLC 1200 series |
| Column | Phenomenex Chirex 4.6 × 150 mm (5 μm) |
| Mobile Phase | 85% 3 mM $CuSO_4$, 15% MeOH |
| Flow Rate | 1.00 mL/min |
| Detection Wavelength | 254.0 nm |
| Detector Temperature | 25° C. |
| Injection Volume | 10 μL |
| Run time | 20.0 min |
| Retention Times: | Peak 1 (L-tert-leucine): 11.319 min |
| | Peak 2 (D-tert-leucine): 19.560 |

Example 2: 800 Gram-Scale Biocatalytic Process for Preparation of Enantiomerically Pure L-Tert-Leucine from Trimethylpyruvic Acid (TMP)

This Example illustrates a scaled up version of the biocatalytic process for production of enantiomerically pure L-tert-leucine from trimethylpyruvic acid as described in Example 1 to near-kilogram scale. Generally, the reaction protocol followed the same general scheme described in Example 1, only at a larger scale.

The materials used and their sources are provided in Table 11.

TABLE 11

| Material | Quantity |
|---|---|
| Trimethyl pyruvate (TMP) | 800 g |
| Ammonium formate | 128 g |
| Ammonia (25% w/w) | 750 mL |
| Isopropanol (IPA) | 800 mL |
| NAD | 4 g |
| LeuDH (SEQ ID NO: 26) | 12 g |
| KRED (SEQ ID NO: 18) | 12 g |
| Deionized water (DIW) | 5.5 L |
| Acetone | 11 L |
| Celite 545 | 250 g |

Reaction Protocol

A 10 L two neck round bottom flask in a water bath was charged 800 g TMP substrate in ~5 L water. Overhead stirrer (equipped with flat two-blade paddle; 8 cm diameter) was started and water bath heated to 40.0° C. The ammonia was added in portions until all TMP was dissolved (approx. temperature increase of 4° C.). The flask was then charged ammonium formate and IPA. The pH was adjusted with ~170 mL ammonia to pH 9.0±0.1 at 40.0° C.±0.5° C. The solution was charged with 12 g of KRED of SEQ ID NO: 18, 12 g of LeuDH of SEQ ID NO: 26, and 4 g of NAD in 500 mL water. The reaction volume was adjusted to 8 L with water as necessary. After 18 h the reaction was complete (as determined by Method 1 analysis of Example 1).

Workup Procedure

Charged 250 g Celite 545 and stir for about 15 min then filtered off Celite with a 5 L P4 fritted funnel. Distilled off ammonia, acetone, IPA and water at 50° C. under reduced pressure up to 60 mbar, until a vessel volume of ~2.5 L is achieved. Charged residue in a 15 L bucket with 10 L cold acetone (4 vols) and mixed for 5 min. Closed bucket was stored overnight at 4° C. Precipitate was filtered off and washed two times with 500 mL cold acetone. Filter cake was dried at 50° C. under reduced pressure yielding 624 g L-tert-Leucine as a beige powder having >95% e.e.

The crude beige powder from this workup procedure could be immediately used in the reaction with the N-protecting groups MOC or BOC as described in Example 3, to produce the N-protected version of L-tert-leucine.

Example 3: Preparation of MOC-Protected L-Tert-Leucine

This Example illustrates a process for production of a MOC-protected L-tert-leucine compound made using L-tert-leucine prepared biocatalytically using LeuDH and an engineered KRED recycling system as described in Examples 1 or 2.

Materials used in the process are shown in Table 12.

TABLE 12

| Material | Quantity |
|---|---|
| L-tert-Leucine | 10.0 g |
| Deionized water (DIW) | 80 mL |
| Methyl chloroformate (MOC-Cl) | 14.4 g |
| NaOH, 50% wt/wt aqueous | 21.4 g |
| Hydrochloric acid, 12N | 12 mL |
| Isopropyl acetate (iPrOAc) | 8.0 mL |
| Heptane (Hept) | 125 mL |
| Ethyl acetate (EtOAc) | 120 mL |
| NaCl, saturated aqueous | 10 mL |

Equipment and Reaction Protocol

A 300 mL round-bottomed flask fitted with a mechanical stirrer, thermocouple, and graduated addition funnel was used for the reaction, extractive workup. Temperature was controlled with a water/ice bath for below ambient temperature and a calibrated pH probe and meter used at certain stages. For isolation the vessel was fitted with a short-path distillation head.

The reaction vessel was charged with 10.0 g crude L-tert-Leucine (e.g., made as in Example 2) and 70 mL water, and the stirrer set at 150 rpm. 21.4 g of NaOH added to the addition funnel and fed dropwise into the reaction over 5 min (temperature remains <35 C) resulting in a straw-colored solution. The addition funnel was rinsed with 10 mL water and then charged with 14.4 g MOC—Cl, 14.4 g. The MOC—Cl was fed into the reaction dropwise over 30-40 min (temperature does not exceed 50° C.). HPLC was used to monitor the reaction for completion of conversion.

Workup Procedure

Upon complete conversion a pH probe was inserted and the flask allowed to cool <25 C. Approximately 12 mL of 12 N HCl was fed drop wise using the addition funnel until the pH was ~2 while keeping the temperature <30° C. The reaction was charged with 60 mL ethyl acetate which was mixed for 2 min and then layers allowed to separate (emulsions were filtered through an "M" sintered frit). The upper organic layer was removed and stored. The pH was re-adjusted to ~pH 3 and the extraction was repeated two more time with 40 mL then 20 mL of ethyl acetate. The extracted upper organic layers were combined and charged the 10 mL saturated NaCl with mixing for 2 min followed by layer separation. The organic layers (~130 mL) were charged to a reaction vessel fitted with a distillation kit. Heat was applied to distill solvent (with 200 rpm stirring) until a vessel volume of 80 mL is achieved. Continue distillation with heptane fed dropwise to maintain ~80 mL vessel volume.

Continue distillation and feed until the pot temperature is ~98.2 C. Cool to 80° C. and feed iPrOAc, 8 mL. Cool to 65° C. and charge product seed crystals, 0.1 g. Slowly cool to ambient and then to 5 C. Collect product by filtration on an "M" sintered glass funnel; wash through with recycled liquors until all solid is collected. Wash solid with heptane, 15 mL, and suction dry. Vacuum dry to constant weight at 40° C.

Analytical Methods

HPLC was utilized for in-process analysis of % conversion and final product quality assay. H-NMR was utilized only for final product quality assay for general purity and as a check for residual solvents.

Sample Preparation:

During the reaction, with mixer on, a 200 μL aliquot is withdrawn via pipette and diluted into 3000 μL of acetonitrile/water (50:50). This sample is shaken by hand to ensure homogeneity. The sample is further diluted 1:2 prior to injection.

The analytical instrumentation and relevant parameters are shown in Table 13.

TABLE 13

| Instrument | Agilent 1100 | | |
|---|---|---|---|
| Column | TOSOH Bioscience, #19533, TSKGel Amide80 (4.6 mm × 10 cm, 5 μm) | | |
| Column temp | 30° C. | | |
| Detection | 205 nm | | |
| Flow rate | 1.2 mL/min | | |
| Mobile phase | C = water; D = acetonitrile | | |
| Timetable: | Time (min) | % C | % D |
| | 0 | 0.2 | 99.8 |
| | 2.00 | 1 | 99.0 |
| | 10.00 | 60 | 40 |
| | 12.00 | 0.2 | 99.8 |
| Injection volume | 10 μL | | |
| Sample Concentration | ~5 mg/mL | | |
| Retention Times | tert-leucine: 7.8 min MOC-tert-leucine: 1.7 min | | |

Example 4: Preparation of BOC-Protected L-Tert-Leucine

This Example illustrates a process for production of a BOC-protected L-tert-leucine compound made using L-tert-leucine prepared biocatalytically using a ketoreductase (KRED) recycling system as described in Examples 1 or 2.

Materials used in the process are shown in Table 14.

TABLE 14

| Material | Quantity |
|---|---|
| L-tert-Leucine | 10 g |
| Deionized water (DIW) | 70 mL |
| Triethylamine (TEA) | 7.71 g |
| di-tert-butyl dicarbonate (BOC$_2$O) | 20.8 g |
| NaOH, 50% wt/wt aqueous | 9.15 g |
| Tetrahydrofuran (THF) | 30 mL |
| Heptane | 285 mL |
| Ethyl acetate | 145 mL |
| NaCl, saturated aqueous | 10 mL |

Equipment and Reaction Protocol

Reaction Vessel:

A 300 mL round-bottomed flask fitted with a mechanical stirrer, thermocouple, and graduated addition funnel was used for the reaction and extractive workup. Temperature was controlled with a water/ice bath for below ambient temperature. A calibrated pH probe and meter was used at certain stages.

Isolation Vessel:

A 500 mL round-bottomed flask fitted with a mechanical stirrer, thermocouple with temperature controller and heating mantle, graduated addition funnel, and distillation kit was used for the solvent exchange and crystallization.

Reaction vessel was charged 10.0 g crude L-tert-Leucine product (as made in Example 2), and 70 mL to the reaction vessel and set stirrer at 150 rpm. Solution was a suspension. Charged TEA, 7.71 g, over 5 min so that T remains <25° C., which resulted in a straw-colored solution. Charged reaction vessel with NaOH, 4.57 g, over 2 min, resulting in an opaque solution. Prepared a solution of BOC$_2$O, 20.8 g., in THF, 30 mL, and fed dropwise to reaction vessel over 30-40 min, without allowing temperature to exceed 32° C. The reaction was monitored for complete conversion by HPLC as described in Example 3, except that retention time for BOC-tert-leucine was 1.5 min.

Workup Procedure

Checked pH and adjusted with 50% NaOH to pH >9.2. Charged vessel with heptanes (30 mL) with mixing. Upper organic layer was removed and a pH probe and flask cooled to <25° C. before charging with ~32 mL 3 N HCl dropwise (pH ~3.5) and keeping temperature <30° C. Remove cooling and charged with ethyl acetate (50 mL) followed by mixing for 2 min and removal of upper organic layer. pH was readjusted to ~3.5, if necessary, and the vessel charged with ethyl acetate (70 mL) and heptane (30 mL). Upper organic layer removed and stored. Charged again with ethyl acetate (25 mL) and heptane (25 mL). Upper organic layer removed and stored. All organic phases were combined and filtered through an "M" sintered frit if an emulsion were present.

The combined organic phases were charged with sat'd NaCl, 10 mL, mixed for 2 min and allowed to separate. Lower layer was removed (~235 mL) and charged to a crystallizer fitted with a distillation kit. Heat was applied to distill solvent until a vessel volume of 100 mL is achieved. Continue distillation and begin feeding heptanes dropwise so as to maintain ~100 mL vessel volume. Continue distillation and feed until the pot temperature ~98° C. Cool to 5° C. and collect product by filtration on an "M" sintered glass funnel. Wash through with recycled liquors until all solid is collected. Wash solid with pre-cooled (5° C.) heptane, 15 mL. Vacuum dry to constant weight at 40° C.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A process for converting a compound mixture of formula IId which comprises a substrate for an amino acid dehydrogenase to a composition of formula I and a chiral amino acid of formula IIa:

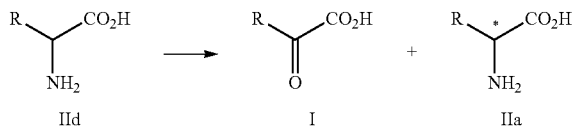

comprising contacting the compound mixture of formula IId with an enantioselective D-amino acid dehydrogenase, wherein said D-amino acid dehydrogenase is a D-alanine dehydrogenase, in a reaction medium comprising NAD$^+$/NADH or NADP$^+$/NADPH and a cofactor recycling system comprising a ketoreductase, wherein said ketoreductase comprises a polypeptide sequence at least 90% identical to SEQ ID NO:18, and a lower alkyl ketone, under conditions where the compound mixture of formula IId is converted to the composition of formula I and a chiral amino acid of formula IIa, and the lower alkyl ketone is converted to a lower secondary alcohol; wherein R is a substituted or unsubstituted —(C$_1$-C$_{10}$)alkyl, —(C$_2$-C$_6$)alkenyl, —(C$_2$-C$_6$)alkynyl, —(C$_3$-C$_8$)cycloalkyl, heterocycloalkyl, aryl, or heteroaryl.

2. The process of claim 1, wherein the compound mixture of IId is a racemic mixture of formula IIe:

3. The process of claim 1, wherein the chiral amino acid of formula IIa is IIc

wherein the chiral amino acid of formula IIc is present in enantiomeric excess.

4. The process of claim 3, wherein the D-amino acid dehydrogenase is from *Bacillus, Clostridium, Corynebacterium, Geobacillus, Natronobacterium, Synechocystis, Thermoactinomyces, Thermos, Thermomicrobium,* or *Carderia*.

5. The process of claim 1, wherein the chiral amino acid of formula IIa is IIb

wherein the chiral amino acid of formula of formula IIa is present in enantiomeric excess.

6. The process of claim 5, wherein the D-amino acid dehydrogenase is from *Halobacterium, Methanosarcina, Pseudomonas, Pyrobaculum, Salmonella, Corynebacterium,* and *Escherichia*.

7. The process of claim 6, wherein the D-amino acid dehydrogenase is from *Pseudomonas aeruginosa, Pseudomonas fluorescens, Pyrobaculum islandicum, Salmonella typhimurium, Corynebacterium glutamicum,* and *Escherichia coli*.

8. The process of claim 1 which is carried out in a cell free system.

9. The process of claim 1, wherein the D-amino acid dehydrogenase is present as a crude extract.

10. The process of claim 1, wherein the D-amino acid dehydrogenase is substantially purified.

11. The process of claim 1, wherein the ketoreductase is from *Lactobacillus, Candida, Novosphingobium*.

12. The process of claim 11, wherein the ketoreductase of *Novosphingobium* is from *Novosphingobium aromaticivorans*.

13. The process of claim 1, wherein the ketoreductase is an engineered ketoreductase characterized by increased thermostability, increased solvent stability, and/or increased enzymatic activity relative to the wild type ketoreductase.

14. The process of claim 1, wherein the ketoreductase is present as a crude extract.

15. The process of claim 1, wherein the ketoreductase is substantially purified.

16. The process of claim 1, further comprising the step of removing the lower secondary alcohol formed from the lower alkyl ketone from the reaction medium.

17. The process of claim 1, wherein the lower alkyl ketone is acetone and the lower secondary alcohol is isopropanol.

18. The process of claim 17, wherein the isopropanol is removed from the reaction medium.

19. The process of claim 1, wherein the reaction medium is at a pH of about 8.5 to about 10.

20. The process of claim 19, wherein the reaction medium is at a pH of about 8.5 to about 9.0.

21. The process of claim 1, wherein the reaction medium is at a temperature of about 25° C. to about 45° C.

22. The process of claim 21, wherein the reaction medium is at a temperature of about 35° C. to about 40° C.

23. The process of claim 1, wherein the lower alkyl ketone is present in at least 1.5 fold stoichiometric excess of the substrate of formula IIc.

* * * * *

UNITED STATES PATENT AND TRADEMARK OFFICE
CERTIFICATE OF CORRECTION

PATENT NO. : 10,196,667 B2
APPLICATION NO. : 15/627652
DATED : February 5, 2019
INVENTOR(S) : Cabirol et al.

Page 1 of 1

It is certified that error appears in the above-identified patent and that said Letters Patent is hereby corrected as shown below:

In the Claims
In Claim 11,
Column 80, Line 26, please delete "Lactobacillus, Candida,".

Signed and Sealed this
Nineteenth Day of March, 2019

Andrei Iancu
*Director of the United States Patent and Trademark Office*